US012688919B2

(12) United States Patent
Utz et al.

(10) Patent No.: US 12,688,919 B2
(45) Date of Patent: Jul. 21, 2026

(54) SYSTEMS AND METHODS FOR AUTHENTICATING MEDICAL INFUSION LINES

(71) Applicant: CHS HEALTHCARE VENTURES, INC, Decatur, GA (US)

(72) Inventors: Hans Utz, Decatur, GA (US); Dragan Nebrigic, Austin, TX (US)

(73) Assignee: CHS Healthcare Ventures, Inc, Decatur, GA (US)

( * ) Notice: Subject to any disclaimer, the term of this patent is extended or adjusted under 35 U.S.C. 154(b) by 1151 days.

(21) Appl. No.: 17/578,761

(22) Filed: Jan. 19, 2022

(65) Prior Publication Data

US 2022/0230725 A1 Jul. 21, 2022

Related U.S. Application Data

(60) Provisional application No. 63/138,961, filed on Jan. 19, 2021.

(51) Int. Cl.
*G16H 20/17* (2018.01)
*A61M 5/14* (2006.01)
(Continued)

(52) U.S. Cl.
CPC .............. *G16H 20/17* (2018.01); *A61M 5/14* (2013.01); *A61M 5/1582* (2013.01);
(Continued)

(58) Field of Classification Search
CPC . G16H 20/17; A61M 5/14; A61M 2205/3306; A61M 2205/3317;
(Continued)

(56) References Cited

U.S. PATENT DOCUMENTS

| 5,041,086 A | 8/1991 | Koenig et al. |
| 5,423,750 A | 6/1995 | Spiller |

(Continued)

FOREIGN PATENT DOCUMENTS

| AU | 2007282071 A1 | 2/2008 |
| CN | 102847204 A | 9/2012 |

(Continued)

*Primary Examiner* — Tarifur R Chowdhury
*Assistant Examiner* — Joshua M Carlson
(74) *Attorney, Agent, or Firm* — Bryan L. Baysinger; Maynard Nexsen PC

(57) ABSTRACT

Aspects of systems and methods for authenticating illuminating medical infusion lines are disclosed. In one aspect a method for authenticating medical infusion lines utilizing a cap color detection assembly is disclosed. The method includes provisioning an electronic illuminator for illuminating medical infusion lines with a cap color detection assembly. Next, connecting a side scattering fiber optic cable with a fiber funnel cap that is configured with a visible color with the electronic illuminator. Then, transmitting a white light from the cap color detection assembly and recording reflected light from the fiber funnel cap. Then, converting the recorded reflective light to a color code. In another aspect a method for authenticating medical infusion lines is disclosed utilizing a fiber detection assembly. The method includes provisioning an electronic illuminator for illuminating medical infusion lines with a fiber detection assembly. Then connecting a side scattering fiber optic cable with a fiber funnel cap that is configured with a metallic plate with the electronic illuminator. Next, detecting a change in voltage as the fiber funnel cap of the side scattering fiber optic cable is connected, wherein a final voltage results in a magnetic flux key. Lastly, authenticating, by the MCU on the electronic illuminator, the magnetic flux key with stored parameters.

6 Claims, 17 Drawing Sheets

(51) Int. Cl.

| | |
|---|---|
| *A61M 5/158* | (2006.01) |
| *A61M 5/162* | (2006.01) |
| *A61M 5/172* | (2006.01) |
| *F21V 33/00* | (2006.01) |
| *G02B 6/44* | (2006.01) |
| *G16H 40/63* | (2018.01) |
| *H05B 45/10* | (2020.01) |
| *H05B 47/11* | (2020.01) |
| *A61L 103/15* | (2026.01) |
| *A61M 5/145* | (2006.01) |

(52) U.S. Cl.
CPC ............ *A61M 5/162* (2013.01); *A61M 5/172* (2013.01); *F21V 33/0068* (2013.01); *G02B 6/4442* (2013.01); *G02B 6/4482* (2013.01); *G16H 40/63* (2018.01); *H05B 45/10* (2020.01); *H05B 47/11* (2020.01); *A61L 2103/15* (2026.01); *A61L 2202/14* (2013.01); *A61M 2005/1401* (2013.01); *A61M 2005/14553* (2013.01); *A61M 2205/14* (2013.01); *A61M 2205/3306* (2013.01); *A61M 2205/3313* (2013.01); *A61M 2205/3317* (2013.01); *A61M 2205/3633* (2013.01); *A61M 2205/587* (2013.01); *A61M 2205/6054* (2013.01); *A61M 2205/6081* (2013.01); *A61M 2205/8206* (2013.01); *A61M 2207/00* (2013.01); *F21V 2200/10* (2015.01)

(58) Field of Classification Search
CPC .... A61M 2205/584; A61M 2205/6081; G02B 6/4442; G02B 6/4482; F21V 2200/10; A61N 2005/063
See application file for complete search history.

(56) References Cited

U.S. PATENT DOCUMENTS

| | | | |
|---|---|---|---|
| 5,681,285 | A | 10/1997 | Ford et al. |
| 6,059,768 | A | 5/2000 | Friedman |
| 7,860,583 | B2 | 12/2010 | Condurso et al. |
| 8,679,075 | B2 | 3/2014 | Lurvey et al. |
| 9,501,619 | B2 | 11/2016 | Portnoy et al. |
| 10,232,107 | B2 | 3/2019 | Utz |
| 2007/0106263 | A1 | 5/2007 | Ward |
| 2010/0006171 | A1 | 1/2010 | Tomlin et al. |
| 2011/0196306 | A1 | 8/2011 | De La Huerga |
| 2011/0264463 | A1 | 10/2011 | Kincaid et al. |
| 2013/0123579 | A1 | 5/2013 | Adams et al. |
| 2014/0036276 | A1* | 2/2014 | Gross .................... G01B 11/02 356/402 |
| 2015/0018645 | A1* | 1/2015 | Farkas ................. A61B 5/0077 600/317 |
| 2015/0190649 | A1* | 7/2015 | Gelfand ........... A61M 16/0434 385/100 |
| 2016/0175521 | A1 | 6/2016 | Adams et al. |
| 2017/0014023 | A1 | 1/2017 | Kern |
| 2017/0021095 | A1 | 1/2017 | Utz |
| 2017/0023216 | A1 | 1/2017 | Utz |
| 2017/0258983 | A1 | 9/2017 | Utz |
| 2017/0281855 | A1 | 10/2017 | Utz |
| 2017/0340815 | A1 | 11/2017 | Utz |
| 2018/0177938 | A1 | 6/2018 | Provost et al. |
| 2019/0091398 | A1 | 3/2019 | Utz |
| 2019/0168023 | A1* | 6/2019 | Eltorai ............... A61M 1/3661 |
| 2020/0402228 | A1* | 12/2020 | Talbert ............... A61B 1/2676 |
| 2022/0054738 | A1* | 2/2022 | Pananen .............. A61J 1/1418 |

FOREIGN PATENT DOCUMENTS

| | | | |
|---|---|---|---|
| EP | 1157711 | A2 | 5/2008 |
| EP | 2009533 | A1 | 12/2008 |
| WO | 2019164988 | A1 | 8/2019 |

* cited by examiner

1102

1504

1502

SYSTEMS AND METHODS FOR AUTHENTICATING MEDICAL INFUSION LINES

CROSS-REFERENCE TO RELATED APPLICATIONS

This application is related and claims priority to U.S. Provisional Patent Application No. 63/138,961 entitled "Electronic Illuminator" filed on Jan. 19, 2021. This application is also related to and co-filed with utility applications "Assemblies and Subsystems for Electronic Illuminators", "Systems and Methods for Controlling Microorganism Load with an Electronic Illuminator", "Method and Manufacture of a Dual Lumen Fiber Optic Medical Infusion Line", "Medical Infusion Line Electronic Illuminator." The entire disclosure of said applications are incorporated herein by reference.

FIELD

The present invention relates to electronic illumination of fiber optic lines with an electronic illuminator. In particular, systems and methods for authenticating illuminating medical infusion lines.

BACKGROUND

The present disclosure relates generally to systems and methods for improving the administration of medical infusion utilizing illumination along with advanced sensor assemblies and leveraging computational intelligence to advance patient care and reduce practitioner cognitive load. Medical infusion serves to administer medications, fluids, nutrients, solutions, and other materials intravenously to a patient. Patients are often administered medical infusion using intravenous infusion tubing or lines ('IVT'). Such intravenous infusion tubing generally consist of flexible, polymer tubing connected at one end to a fluid source and at another end to a needle or port assembly that provides access to a blood vessel of a patient. It is not uncommon for many infusion tubes, each connected to a different source of fluid (medical infusion pump), to be used simultaneously to deliver several medications at once to a single patient. It is also not uncommon for the needles or port assemblies to be located adjacent one another, such as multiple adjacent needles providing access into the brachial vein running through the arm of the patient.

Medical infusion tubes have seen little in progress for adapting to modern medical facilities. Practitioners, including nurses, physicians, and others are inundated with information that may come in a variety of forms. On top of this, the high stakes and often rapid response environment leads to medical error. The disclosure herein aims to reduce medical error and to provide a sensible system and method for lowering the cognitive load for practitioners. In this regard verification is required to ensure the system is operating as intended.

Further, medical devices are designed and approved through rigorous testing and compliance with local jurisdictional laws and regulations. It is well known that generic or unauthorized products may become available on the market, which may not possess the same quality or safety standards. Further, such products may also present a danger to the patient or the user. Therefore, the problem of generic or non-compliant materials and devices is solved with an array of sensors, assemblies, processors, physics, utilizing electrical and computational engineering to improve upon and develop advanced systems of an electronic illuminator and side scattering fiber optics to facilitate authentication and verification of equipment utilized in illuminating medical infusion lines.

SUMMARY

Aspects of systems and apparatuses for medical infusion illumination are disclosed herein. In one aspect, a system for authenticating medical infusion line illumination is disclosed. A system of one or more computers (MCUs, processing units, Integrated Circuits) can be configured to perform particular operations or actions by virtue of having software, firmware, hardware, or a combination of such installed on the system that in operation causes or cause the system to perform the actions. One or more computer programs may be configured to perform particular operations or actions by virtue of including instructions that, when executed by data processing apparatus, cause the apparatus to perform the actions. One general aspect includes a system for illuminated medical infusion line authentication, including (i) an electronic illuminator, which may include: a cap color detection assembly. Further, a fiber detection assembly (ii) having a side scattering fiber optic cable, which may include: a fiber funnel cap with a visible color at a proximal end and a metallic plate; and a protective end cap at a distal end. Other embodiments of this aspect include corresponding computer systems, apparatus, and computer programs recorded on one or more computer storage devices, each configured to perform the actions of the methods.

Implementations may include one or more of the following features. The system wherein the fiber detection assembly is configured with a three dimensional magnetic flux density. The fiber detection assembly may include a hall sensor. The fiber detection assembly may also include the use of three magnets and a steel bar. The system may further comprise a cap color detection assembly. The cap color detection assembly of the electronic illuminator, detects color of the fiber funnel cap on the side scattering fiber optic cable. The cap color detection assembly may include a photoelectric sensor. The cap color detection assembly may include a R/G/B sensor. The cap color detection assembly may include a color code band detection, where the fiber funnel cap may include a multiple band color code. Implementations of the described techniques may include hardware, a method or process, or computer software on a computer-accessible medium.

One general aspect includes a method for authenticating medical infusion lines. The method also includes provisioning an electronic illuminator for illuminating medical infusion lines with a cap color detection assembly; connecting a side scattering fiber optic cable with a fiber funnel cap that is configured with a visible color with the electronic illuminator, transmitting a white light from the cap color detection assembly and recording reflected light from the fiber funnel cap, converting the recorded reflective light to a color code, and verifying by an MCU on the electronic illuminator the color code is an approved color code. Other embodiments of this aspect include corresponding computer systems, apparatus, and computer programs recorded on one or more computer storage devices, each configured to perform the actions of the methods.

Implementations may include one or more of the following features. The method may include provisioning a multiple band code on the fiber funnel cap of the side scattering fiber optic cable. The method may include transmitting the white light from the cap color detection assembly and recording reflected light from each band of the multiple band code. The method may include converting the multiple band code to a color code. The method may include verifying by the MCU on the electronic illuminator the multiple band color code is an approved color code. The method may include alerting by the electronic illuminator that the side scattering fiber optic cable is authentic. Implementations of the described techniques may include hardware, a method or process, or computer software on a computer-accessible medium.

One general aspect includes a method for authenticating medical infusion lines. The method also includes provisioning an electronic illuminator for illuminating medical infusion lines with a fiber detection assembly; connecting a side scattering fiber optic cable with a fiber funnel cap that is configured with a metallic plate with the electronic illuminator; detecting a change in voltage as the fiber funnel cap of the side scattering fiber optic cable is connected, where a final voltage results in a magnetic flux key; and authenticating, by an MCU on the electronic illuminator, the magnetic flux key with stored parameters. Other embodiments of this aspect include corresponding computer systems, apparatus, and computer programs recorded on one or more computer storage devices, each configured to perform the actions of the methods.

Implementations may include one or more of the following features. The method may include alerting by the electronic illuminator that the side scattering fiber optic cable is authentic. The method may include alerting by the electronic illuminator that the side scattering fiber optic cable is not authentic, and further disengaging an LED assembly on the electronic illuminator. Detecting a change in voltage detects an increase in voltage as the fiber funnel cap connects with the electronic illuminator. Provisioning an electronic illuminator with a fiber detection assembly provisions three magnets and a steel bar to calibrate a specific three dimensional magnetic field. Implementations of the described techniques may include hardware, a method or process, or computer software on a computer-accessible medium.

BRIEF DESCRIPTION OF THE DRAWINGS

Many aspects of the present disclosure will be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views. It should be recognized that these implementations and embodiments are merely illustrative of the principles of the present disclosure. Therefore, in the drawings.

DETAILED DESCRIPTION

Figure 1A:
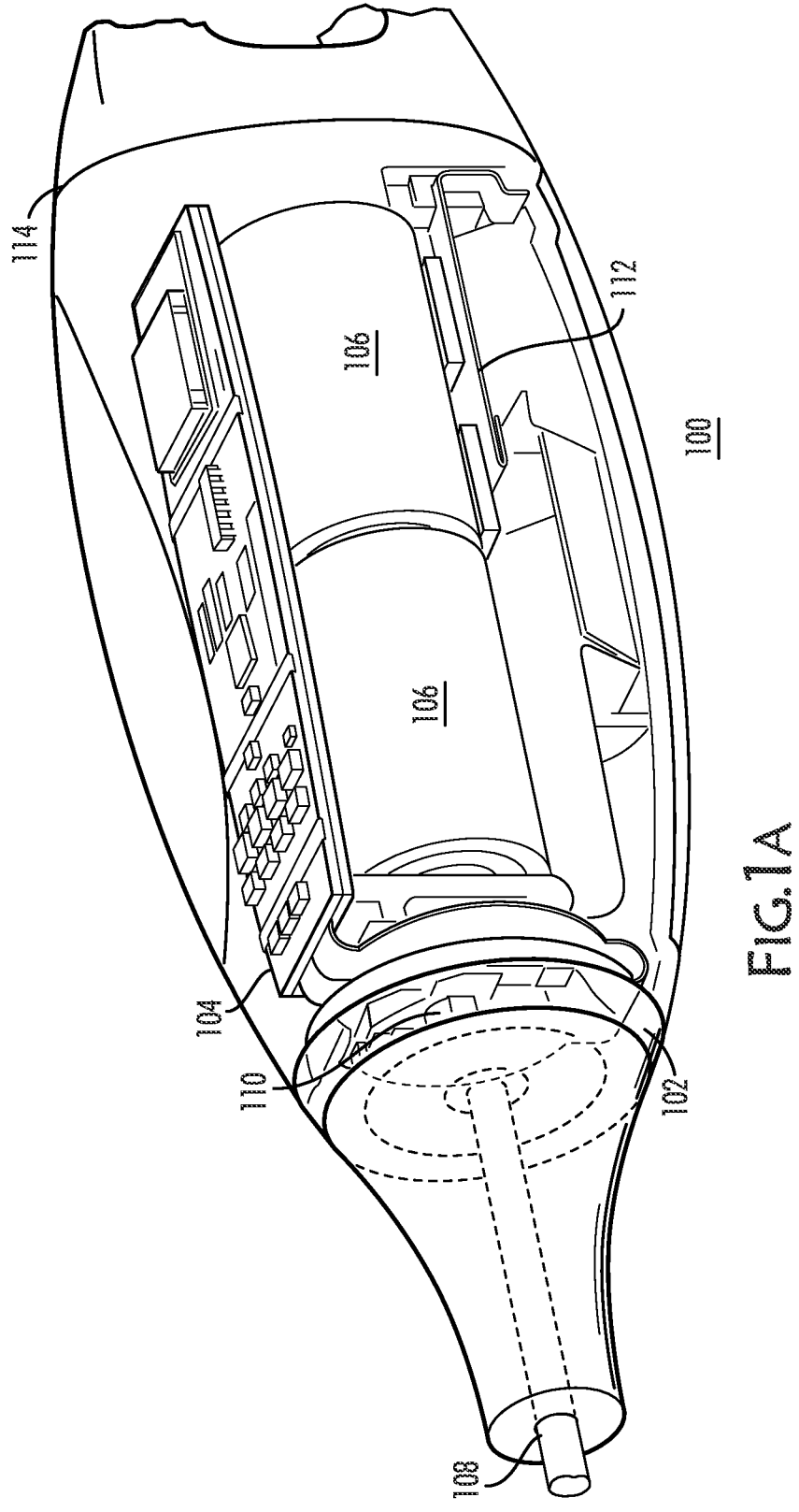
FIG. 1A is perspective view of an illustration of an example electronic illuminator, displaying the configuration of internal components and subsystems.

The presently disclosed subject matter now will be described more fully hereinafter with reference to the accompanying drawings, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated drawings. Therefore, it is to be understood that the presently disclosed subject matter is not to be limited to the specific embodiments disclosed and that modifications and other embodiments are intended to be included within the scope of the appended claims.

Throughout this specification and the claims, the terms "fiber optic cable," "fiber optic line," and "fiber optic" are used to mean a side scattering or side emitting or side glow fiber optic cable, wherein light or illumination is purposefully emitted as it traverses the length of the cable or line.

Throughout this specification and the claims, the terms "comprise," "comprises," and "comprising" are used in a non-exclusive sense, except where the context requires otherwise. Likewise, the term "includes" and its grammatical variants are intended to be non-limiting, such that recitation of items in a list is not to the exclusion of other like items that can be substituted or added to the listed items.

I. Example Use Case Scenarios

Medical infusion serves to administer medications, fluids, nutrients, solutions, and other materials intravenously to a patient. Patients are often administered medical infusion using intravenous infusion tubes or lines ('IVT'). Such intravenous infusion tubes generally consist of flexible, plastic tubing connected at one end to a fluid source and at another end to a needle or port assembly that provides access to a blood vessel of a patient. It is not uncommon for many infusion lines, each connected to a different source of fluid (medical infusion pump), to be used simultaneously to deliver several medications at once to a single patient. It is also not uncommon for the needles or ports to be located adjacent one another, such as multiple adjacent needles providing access into the brachial vein running through the arm of the patient.

Distinguishing between multiple infusion lines is a difficult task that is placed in an atmosphere of high stress and rapid timing. The medical industry refers to the atmosphere as placing a high cognitive load on practitioners. This high cognitive load can lead to medication delivery error as a result of improperly distinguishing one medical infusion line from another. Arguably, the confusion of one medical infusion line from another is one of the leading causes of preventable medication error. As a result of the difficulties in distinguishing between multiple medical infusion lines and their associated fluid sources and outputs, as well as the potentially life-threatening possibilities that can occur if incompatible medications are injected through the same medical infusion line, there is a need for accurate identification of medical infusion lines.

Medical devices, such as medical infusion lines are subject to rigorous testing and compliance measures. Most often they are delivering lifesaving medicines, fluids, and nutrients, thus the composition of, along with the process of manufacture must be in compliance with laws and regulations. Authentication is one way to address the usage of non-compliant or otherwise non-genuine equipment. Incorrectly manufactured medical infusion lines or systems and methods disclosed herein may cause severe injury to a patient. Thus the ability to authenticate and identify correct devices herein, and the usage, is of significant importance. Thus, the disclosure herein provides systems and methods for authenticating and verifying products and devices utilized in illuminating medical infusion lines.

II. Systems and Methods

In one aspect, a system for illuminated medical infusion line authentication is disclosed. Wherein the system comprises an electronic illuminator with a cap color detection assembly and a fiber detection assembly. The cap color detection assembly may comprise an R/G/B sensor and provide analog to digital conversion of received information from a fiber funnel cap configured to a side scattering fiber optic cable. The side scattering fiber optic cable being equipped with the fiber funnel cap with a visible color at a proximal end and a metallic plate. The visible color may be associated with a color code or R/G/B value, or Hex code or HSL code, so as to identify the particular color. The identified color, from the reflected light from a photoelectric sensor, is then converted to a digital signal, either by the cap color detection assembly onboard computing module or through the MCU on the electronic illuminator, through an analog to digital converter, and the received color may then be used to authenticate based on authorized color codes or values. For example, R/G/B value 229, 42, 1 which is a red color, may be authenticated with the system, other variations of red would identify as non-genuine and the system would alert an error on usage. There may also be a variation of several degrees in either direction on the reading to allow for acceptance of a range to handle irregularities in the manufacture of the cap or funnel cap.

Continuing, with the example of the cap color detection assembly, the proximal end having a fiber funnel cap with ridges on a nodule that is placed within or designed to configure with the housing of the electronic illuminator. The fiber funnel cap being configured to place the side scattering fiber optic line near the lens and LED element of the electronic illuminator. The nodule may have a multiple band code or other code such as a SKU or QR code that may be sensed or read by the cap color detection assembly. In this regard the cap color detection assembly may have an R/G/B sensor along with an optical sensor or laser sensor. In reading it may instruct a color as well as authentication and verification of genuine side scatter fiber optic cables. At the distal end of the side scattering fiber optic cable is a protective end cap. The protective end cap may be made from a polymeric material with a polished or painted inside or a laminate or spray added to increase reflectivity. In this regard, light transferred from the electronic illuminator is reflected at the distal end, and may even return signals, such as pulses or other sequences for identification. For example, a sequence of pulses may be used to identify authentic side scatter fiber optic cables, wherein the illuminator may pulse a coded sequence and wait for the reflection from the polished surface or reflective surface of the distal end cap of the side scatter fiber optic line. If the pulsed sequence is modified from what is expected the electronic illuminator may alert through an error message or sound or otherwise not enable the LED power drivers.

Further, the pulses may be used to determine the length of the fiber optic cable for suitability for a given arrangement. In this regard, pulses may be transmitted down the length of the fiber and returned by bouncing off the protective end cap, the measured time from pulse to return may allow for cable length determination as well as strength of the lux transmitted. In other aspects, the power of the LED power driver may be maintained by the amount of lux returned from the protective end cap on the side scattering fiber optic line.

In another aspect, a fiber detection assembly is configured to an electronic illuminator for authentication and verification. The fiber detection assembly may be configured with a three dimensional magnetic flux density. This may include three magnets positioned to create a specific magnetic flux density or field. Further, the field may be altered by the use of a steel bar or other magnets or metals that may disrupt or alter the three dimensional field. This field is utilized with a hall effect sensor and a metal plate on the funnel cap or fiber side cap or end cap that is inserted into the electronic illuminator to form a flux key or signature. This unique signature is then verified by a processing unit, after being converted to a binary signal and is then matched with a stored parameter or reference value of expected flux key or signature. Therein allowing for verification of the side scattering fiber optic lines by usage of magnetic fields and a fiber detection assembly.

In another aspect, a method for authenticating medical infusion lines is disclosed. In the method an electronic illuminator is provisioned, for example FIGS. 1A-B, for illuminating medical infusion lines, the illuminator configured with a cap color detection assembly. In order to illuminate the medical infusion line, the side scattering fiber optic cable is connected by plugging into or configuring to the end of the electronic illuminator a funnel cap or fiber side end cap, to the electronic illuminator where a lens and LED are positioned.

In another aspect, a method for authenticating medical infusion lines is disclosed. In the method an electronic illuminator is provisioned, for example FIGS. 1A-B, for illuminating medical infusion lines, the illuminator comprising a fiber detection assembly. The example method includes connecting a side scattering fiber optic cable with a funnel cap that is configured with a metallic plate. The metallic plate is utilized with the magnetic flux density of the fiber detection assembly to register a signature or flux key that is tuned to a parameter that can be cross referenced or verified by the electronic illuminator's MCU. This flux key or signature is detected by a hall effect sensor positioned on the PCB of the electronic illuminator that detects a change in voltage when the funnel cap with the magnetic plate is attached, or connected. Thus, the connected side scattering fiber optic line in coordination with the fiber detection assembly authenticates the usage of the side scattering fiber optic line by verifying the flux key or signature matches a stored parameter or range. Further, the electronic illuminator may alter or otherwise signal that the incorrect side scattering fiber optic line is attached, or that the product is not authentic. The electronic illuminator then may turn off the power LED drivers and other items so as to not cause medical error and prevent misuse or risk to a patient.

In one aspect, the LED is configured to the electronic illuminator and is controlled through a printed circuit board ('PCB'). In the example of FIG. 1A, the PCB is a Rigid-Flex PCB ('RF-PCB') (herein also referred to generally as a 'PCB' as PCB's may come in a variety of configurations and materials) (See FIG. 19 for an example) wherein part of the board is rigid and the other part is defined within a flexible ribbon, thus allowing for applications such as within the electronic illuminator housing as disclosed herein. The electronic illuminator is configured to illuminate a fiber optic cable having a proximal end with a cap and a terminal end that terminates in a reflective cap. The fiber optic may be side glow, side scattering, or side emitting, fuzzy fiber optic cable that allows light to emanate or leak to the outside, causing a glow or luminescence.

The electronic illuminator, in one aspect, comprises a housing (See FIGS. 20, 21), along with a rigid-flex PCB or RF-PCB or PCB, and a power source. The housing may be comprised of a polymeric material and have various metal or other heat transferring locations, effectively forming external heat sinks within the housing that connects to an internal heat sink. Further, in other aspects, the housing may be comprised of metal or a blend of polymeric material and a metal, thus forming a protective enclosure for the various assemblies and subsystems. In one aspect the housing allows the electronic illuminator to be water tight or dust proof, and in other aspects it may be rated for waterproofing for a certain period of time at specific atmospheric pressure. Rubber gaskets may align the surfaces of the housing, as well as rubber material for grip, such as textured rubber where a user may come into contact with the electronic illuminators housing. The rubber gaskets assist in water proofing, vibration, dust proofing, and may further attribute to ingress protection, allowing some examples to achieve ratings such as IP65, IP66, and IP67.

Returning to the RF-PCB, in one example it may be configured with an ambient light sensor that is operatively configured within the housing of the electronic illuminator. The ambient light sensor may be any number of makes or models, for example, it may be a sensor manufactured by Lite-On™, such as the LTR-329ALS-01. In one aspect, the flexible region of the RF-PCB allows for adjusting and aligning the ambient light sensor to offset from the LED, therefore allowing for detection of whether or not the LED is powered, along with the LED's relative intensity, and detection of environmental lux. These features incorporated with the onboard microcontroller allow for automatic light intensity configuration through the power drivers on the RF-PCB. In another aspect the ambient light sensor converts light intensity to a digital signal, such as lux, thought an analog to digital converter on the sensor, and transmits the lux value to a microcontroller. In another aspect the conversion is processed on a microcontroller on the RF-PCB, and further used to determine behavior of an electronic illuminator. Even further embodiments, the processing may occur on a microprocessor, wherein the microprocessor may be standalone, or it may be incorporated onto the microcontroller unit.

In one aspect, a sensory system for an electronic illuminator to detect the presence and color of a fiber optic cable cap or funnel cap is disclosed. A sensory system comprises various components, assemblies, and configurations disclosed herein. In one example a sensory system is configured to a light source, such as a light emitting diode. An LED is typically comprised of a silicon lens, a ceramic substrate, a thermal pad, a bond layer, an LED chip or microprocessor, a phosphorous layer, and a cathode. The entire construction is typically within a few millimeter package. Typically, several LED chips are packaged together to provide enough luminous flux to serve the purpose of illuminating.

In another aspect, an electronic illuminator is configured with a fiber detection assembly. Wherein the fiber detection assembly is a hall effect sensor or hall sensor. The assembly may be comprised of a plurality of magnets and a steel bar to create a tuned magnetic field, so as to resemble a key or signature that allows detection of fiber insertion into the electronic illuminator. The key or signature may be unique to a fiber line, to a color, or may be coded for other intelligence. The fiber detection assembly further having a three dimensional magnetic flux density based on at least one or more magnets, forming a magnet assembly, configured to a fiber funnel cap.

In additional aspects, a cap color detection assembly is incorporated onto the RF-PCB of an electronic illuminator. Wherein the cap color detection assembly detects the color of the cap, or a funnel cap, or other design enabled to configure into or on an electronic illuminator to direct light along the side emitting fiber optic cable. The cap color detection assembly, in one aspect, may be comprised of an R/G/B sensor, a light emitting component and an integrated circuit or microprocessor. In further aspects, the cap color detection assembly may be positioned towards the light emitting diode, so as to receive the light radiation directly. Additionally, a cap color detection assembly may comprise a color code band detection, wherein the cap comprises a multiple band color code and the cap color detection assembly is capable of scanning the multiple band code and returning instructions, such as the color the band is coded for or additionally, whether the code also instructs things such as sound, illuminance patterns, or other system alerts.

In additional aspects, an ambient light sensor, a fiber detection assembly, and a cap color detection assembly are operatively configured to the RF-PCB, also referred to generally as a PCB, in the electronic illuminator. The three subsystems work in coordination, and may rely on one another, for example, the ambient light sensor may work in coordination with the fiber detection assembly to determine if a fiber optic cable is present, or if it has illumination running through it. Such procedures may be used to detect a failure in the fitting of the fiber optic line, or may also detect unauthentic, or not genuine configurations.

Referring now to additional aspects of the electronic illuminator. In one aspect the housing may be further comprised of a heat sink. The heat sink may be metal based or based from other transferable materials that allow the dissipation of heat energy from the LED, the power drivers, the microcontroller, and the various microprocessors onboard an example system. Furthermore, the heat sink may be aligned with the power source, such as a battery. The battery may comprise any number of chemistries that are available to provide durational power support for the electronic illuminator.

Referring to methods herein, in one aspect a method for detecting the presence of a fiber in an electronic illuminator is disclosed. In one aspect, the method comprises provisioning an electronic illuminator with an ambient light sensor and a fiber detection assembly. Wherein the ambient light sensor is configured to receive light from outside of the electronic illuminator, thus its configuration on the back side of the RF-PCB allows for diffused exterior light to be acquired through a translucent ring on the exterior housing of the electronic illuminator. Next, the ambient light sensor or microcontroller unit acquires the light intensity and coverts it to a digital signal (lux). Next, the MCU determines the lux based on the digital signal. Then the hall effect sensor on the fiber detection assembly acquires a magnetic flux density. The MCU then determines a tesla value based on the magnetic flux density. Through the hall effect sensor and the ambient light sensor, the presence of a side emitting fiber optic cable may be detected with a digital signal and tesla value, or may be detected independently by either assembly or sensor. Further, when acquiring a magnetic flux density through the hall effect sensor on the fiber detection assembly, the strength of the magnetic flux may be represented based on output voltage. Lastly, the example aspect discloses alerting, by the electronic illuminator, that a fiber optic cable is present. Further, the electronic illuminator may use the subsystem for authenticating that the fiber optic cable is authentic for use with the electronic illuminator based on tesla value alone or in combination with cap color detection assembly.

III. With Reference to Figures

Referring now to FIG. 1A, a perspective view of an illustration of an example electronic illuminator, displaying internal components and subsystems. In the example, an electronic illuminator 100 is disclosed with a fiber funnel cap that may also be referred to as a fiber cap or funnel cap. The fiber funnel cap, in the example, may be of a specific color, wherein when inserted into the receiving unit of the electronic illuminator 100, the color is detected and the electronic illuminator 100 is set to illuminate the LED driver corresponding to cap color. This feature reduces cognitive load as it is intuitive, wherein a red cap will configure the electronic illuminator 100, through an MCU, to display a red light down the fiber optic line 108. In this example, the fiber optic line 108 being a side emitting or side scattering fiber optic line, or one with poor transmission that allows light filter outside of the directionality of the line.

Continuing, in the example, a RF-PCB 104 is disclosed, wherein the flex portion is folded unto itself, forming a location for the R/G/B sensor of a cap color detection system. The folds allow for blocking of the ambient light sensor from the onboard LED of the electronic illuminator, wherein the ambient light sensor acquires environmental lux from the clear housing, also referred to as a translucent ring 102, at the proximal end of the electronic illuminator 100. In other aspects the translucent ring 102 may be opaque or may have a window in it that allows for environmental light. In further embodiments the light from the side emitting fiber optic line may be used to determine environmental lux. Additionally, the magnets supplied for the hall effect sensor forming the fiber detection assembly are embedded within the translucent ring 102, or positioned near the translucent ring 102, to form a magnetic field.

A battery 106 is disclosed along with an internal heat sink 112, wherein the battery powers the electronic illuminator's various assemblies and the internal heat sink 112 works to dissipate heat to the external heat sink on the housing. An LED assembly 110 is positioned to connect with the fiber funnel cap to project light through the side emitting fiber optic line 108. An end cap 114 to the electronic illuminator holds the batteries in place and may further house a communications module or assembly as well as an antenna. With regard to the battery 106, the electronic illuminator, in one aspect, may work in coordination with the ambient light sensor and the cap color detection assembly or the fiber detection assembly to regulate usage of power and to form a swarm of sensors for intelligent power management. In one aspect, the ambient light sensor detects lux in the environment and controls LED power output from the power driver to conserve energy. Further, the cap color detection assembly may detect the fiber funnel cap is not engaged and thus automatically turn the system off. Similarly, the fiber detection assembly may detect an absence of a fiber and a fiber funnel cap, therefore turning the power off until the fiber funnel cap is attached.

Figure 1B:
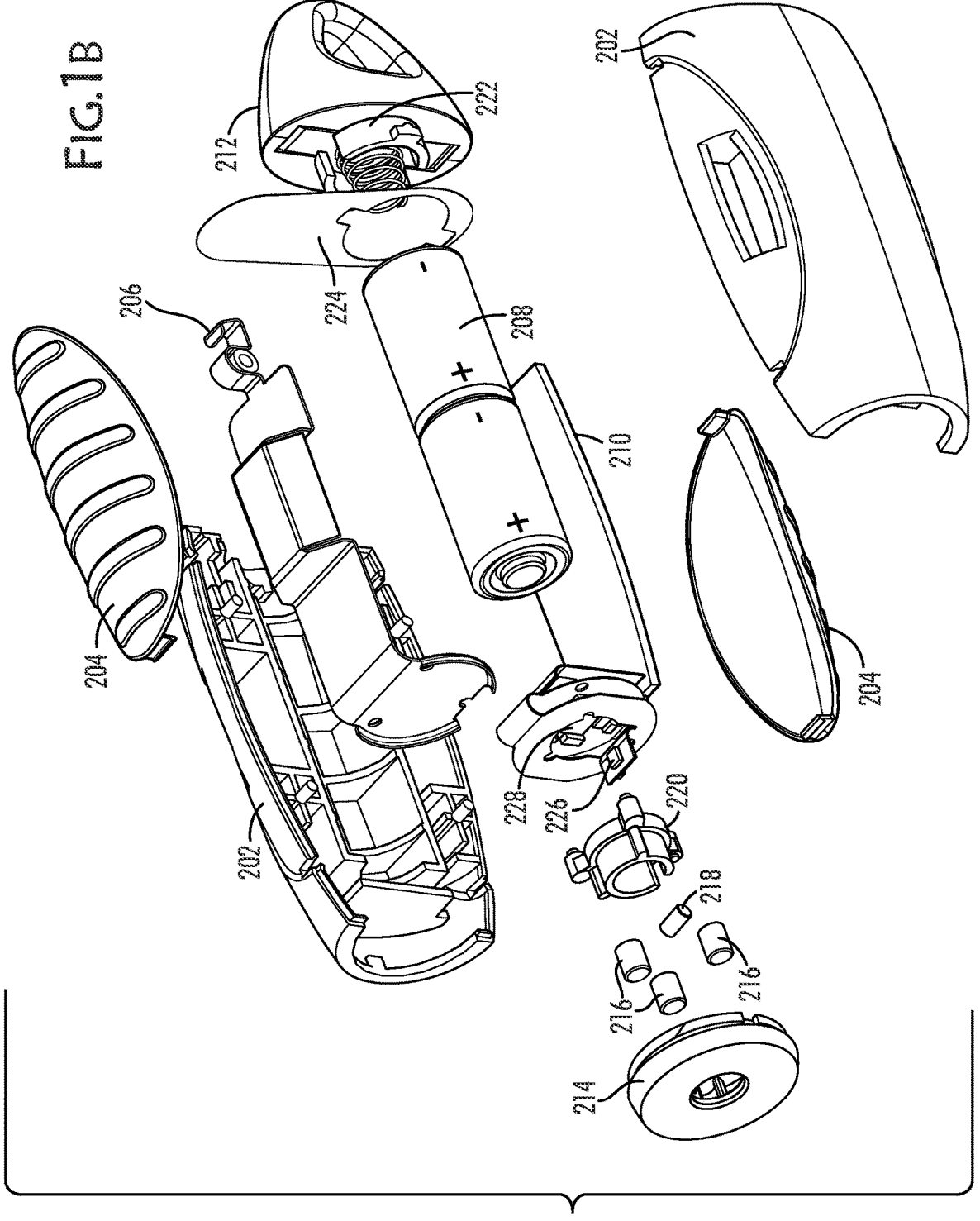
FIG. 1B is an exploded view of an illustration of an example electronic illuminator.

Referring now to FIG. 1B, an exploded view of an illustration of an example electronic illuminator. In the example a housing 202 has locations for an external heat sink 204, wherein the external heat sink 204 is in thermal connection with an internal heat sink 206. The internal heat sink 206 is designed to contact equipment such as the LED power drivers, the LED, and other integrated circuits or microcontrollers, including processing units, so as to reduce heat build-up and control thermals within the tight enclosure. The housing of the example electronic illuminator is further configured with an end cap 212, the end cap having a negative terminal 222. The end cap 212 secures the batteries in place and allows for rapid exchange of batteries. In the example, the end cap 212 has split paper 224 to separate the contact of the batteries and allow for an extended shelf life of the electronic illuminator. Additionally, a translucent ring 214 forms the proximal end or end nearest the fiber optic line, wherein the translucent ring 214 allows light to reach an ambient light sensor. Similarly, in additional embodiments a window to the environment may be provided, wherein the translucent ring is opaque or not translucent and a window within the ring may allow for observing the lux within the environment.

Various examples disclosed herein contain reference to the electronic illuminator, and are identified in FIG. 1B. In one aspect the illuminator is housed within a front shell and a back shell, also referred to as a housing 202. The housing is often made of a polymer but can be made of other materials such as a metal casing. The housing of the electronic illuminator serves to protect the assemblies, sensors, and controllers, as well as provide positioning of said components, and account for size, durability, and ease of transmission of RF signals. An electronic illuminator end cap 212 secures a lithium ion or other battery in place within the shell or housing 202 of the electronic illuminator. The end cap 212 is equipped to receive a piece of split paper 224 to break the current and allow for longer shelf life and storage of the electronic illuminator. In additional aspects an internal heat sink 206, which is integrated along the PCB and/or microcontroller on the PCB and battery supply or batteries, the internal heat sink 206 is then connected through a high thermal conductive material to the metal side covers, or external heat sinks 204 to further dissipate heat. In other aspects the metal side cover is fully formed to the internals of the electronic illuminator and provides for a passive environmental cooling complex.

In another aspect of the example of FIG. 1B, power is supplied from a plurality of batteries 208, which may be of lithium chemistry, or other chemistry, to allow for powering an electronic illuminator. Additionally, the electronic illuminator's batteries 208 may be charged wirelessly or through a uniform serial bus connection such as a USB-B, USB-C, or any micro variants thereof. The RF-PCB 210, also known herein as a PCB, contains a microcontroller, along with the various assemblies and sensors. The RF-PCB 210 forms a folded structure to allow for unique positioning of sensors and assemblies so as to allow for optimal operation. In one aspect, the ambient light sensor is formed to the backside of the RF-PCB 210, so that ambient light from the environment, penetrating through the translucent ring 214 is the only perceived light. This allows for automatic adjustment by the MCU for controlling light intensity. For example, if the surrounding environment is dark, the amount of lux produced by the LED can be lower, as the overall system needs do not require a high lux operation, thus conserving battery life and equipment from excess heat and usage.

The LED assembly 228 on the RF-PCB 210 is configured with a lens 220, wherein the lens 220 is situated to receive the fiber for illumination. The fiber side, in one aspect, is equipped with a fiber funnel cap, that configures to the translucent ring 214 and is held in place by a locking mechanism or through magnetic force and use of magnets, via a magnetic assembly 216 configured to the translucent ring 214 or other housing element of the electronic illuminator. The R/G/B sensor 226, comprising the cap color detection assembly, is disclosed facing inwards toward the receiving orifice of the fiber funnel cap. Additionally, the magnet assembly 216, in coordination with the steel bar 218 or steel pin, provides a magnetic flux key or signature that may be utilized for fiber detection, as well as authentication and security. Wherein the electronic illuminator may be configured to authorize use of a signature or flux key. In one aspect, the authorization is performed by storing onboard parameters such as a specific flux key or signature that is the result of a voltage change or voltage that is read and converted within the hall sensor of the fiber detection assembly.

Figure 2:
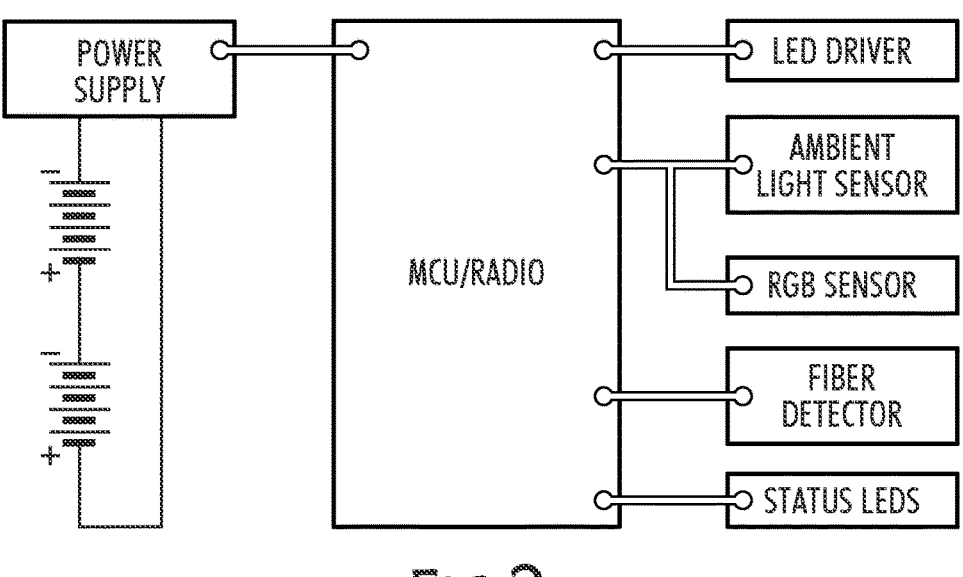
FIG. 2 is a schematic diagram of an example of an electronic illuminator's internal components and subsystems.

Referring now to FIG. 2, a schematic diagram of an example of an electronic illuminator's internal components and subsystems. In one aspect a microcontroller unit or MCU is configured to a power supply such as a battery or may be directly powered through a USB connection to a power source external to the device. Similarly, the power supply may be adapted to receiving power wirelessly through such standards as Qi charging. The schematic of FIG. 2 is an overall generalization of an example of an electronic illuminator, including components such as an LED driver, ambient light sensor R/G/B sensor (which forms a cap color detection assembly), a fiber detection assembly (based in part on a hall sensor), status LED's, and a power supply.

The various components, assemblies, sensors, and subsystems may be in communication utilizing an inter-integrated circuit ('I²C') interface for intra-board communication. Additional communications protocols such as wireless, Bluetooth™, and other radio standards may be additional chipsets configured with the onboard MCU.

Figure 3:
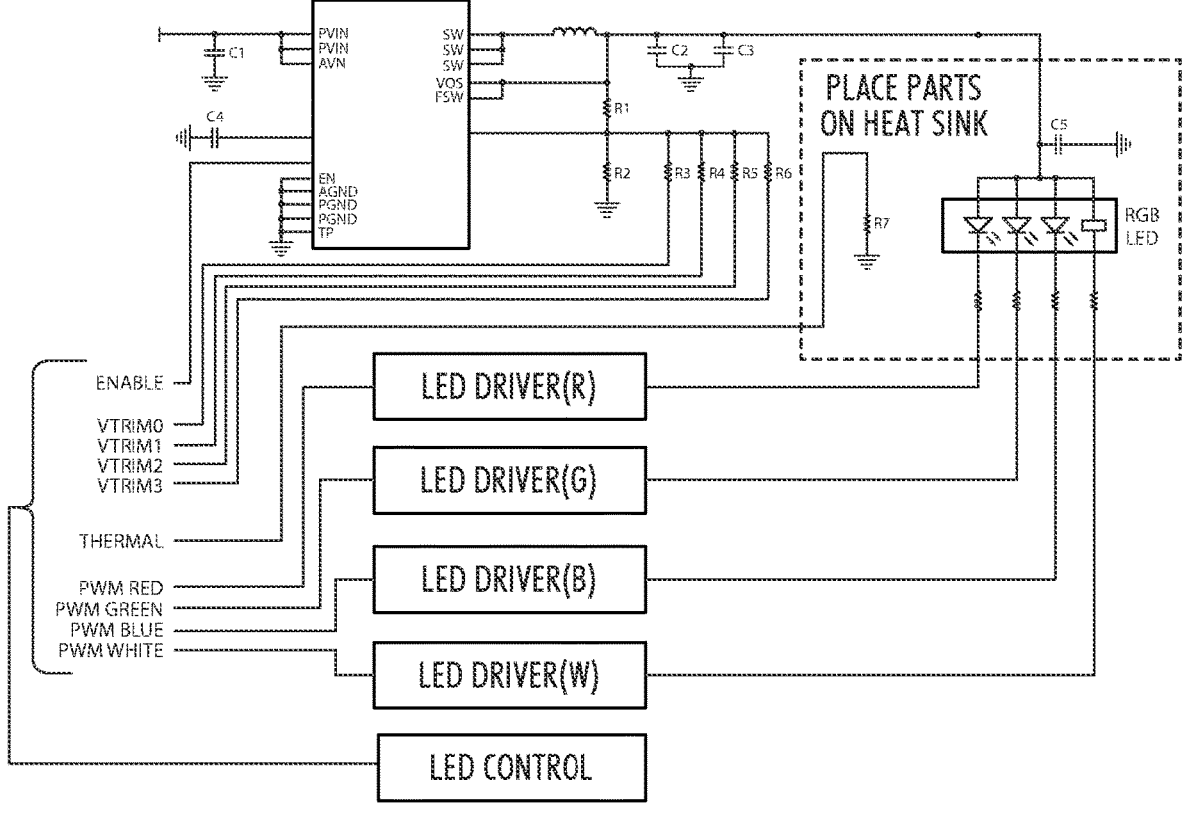
FIG. 3 is a schematic diagram of an example of an electronic illuminator's LED power system drivers.

Turning now to FIG. 3, a schematic diagram of an example of an electronic illuminator's LED power system drivers. In one aspect the power drivers illuminate LED's for varying color frequency. In the disclosed example, a red, green, blue, and white driver powers the various aspects of color. Due to heat or radiance or thermals from the drivers powering the LED components, a heat sink may be applied, such as the one disclosed in FIG. 1B, wherein the heat is diffused along an electronic illuminator, and dispersed exterior thereof through a heat sink mounted externally. Thus, the present embodiment is an internal metallic heat sink in thermal communication with an external facing metallic heat sink. Additional configurations of the LED drivers, as well as LED powering assembly and the chipset are disclosed herein.

Figure 4:
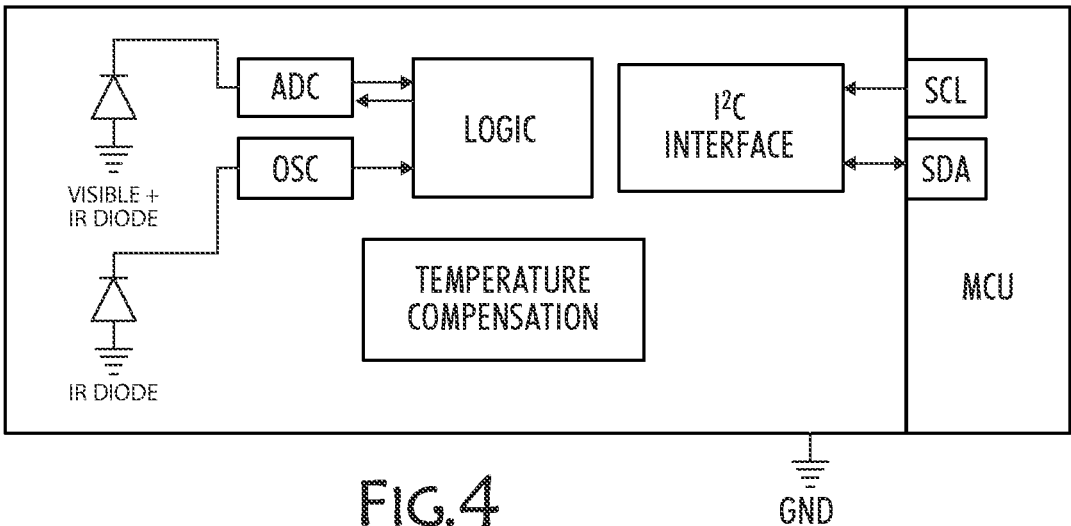
FIG. 4 is a block diagram of an example of an electronic illuminator's ambient light sensor.

Referring now to FIG. 4, a block diagram of an example of an electronic illuminator's ambient light sensor. In one example the ambient light sensor converts light intensity to a digital output signal capable of direct inter-integrated circuit—I²C. With reference to FIG. 4, the Analog to Digital Converter ('ADC'), is configured to the visible IR diode and IR diode, wherein the logic is responsible for converting. Continuing, in the example, the I²C interface is displayed in connection with the Serial Clock ('SLC') and serial data. Thereby, I²C being a synchronous, multi-controller, multi-target, packet switched, single-ended serial communications bus. I²C uses only two bidirectional open collector or open drain lines, serial data line and serial clock line, pulled up with resistors. Typical voltages used are +5 V or +3.3 V, although other voltages are common.

In the example of FIG. 4, operating temperatures are disclosed within a range of 30° Celsius to 70° Celsius, the example ambient light sensor may perceive 6 dynamic ranges from 0.01 lux to 64,000 lux, and automatically reject 50/60 Hz lightings flicker. Thus, in the example, surface mount package, the ambient sensor converts light intensity to a digital output signal that is capable of direct I²C interface with an MCU and other assemblies or components on a PCB.

Figure 5:
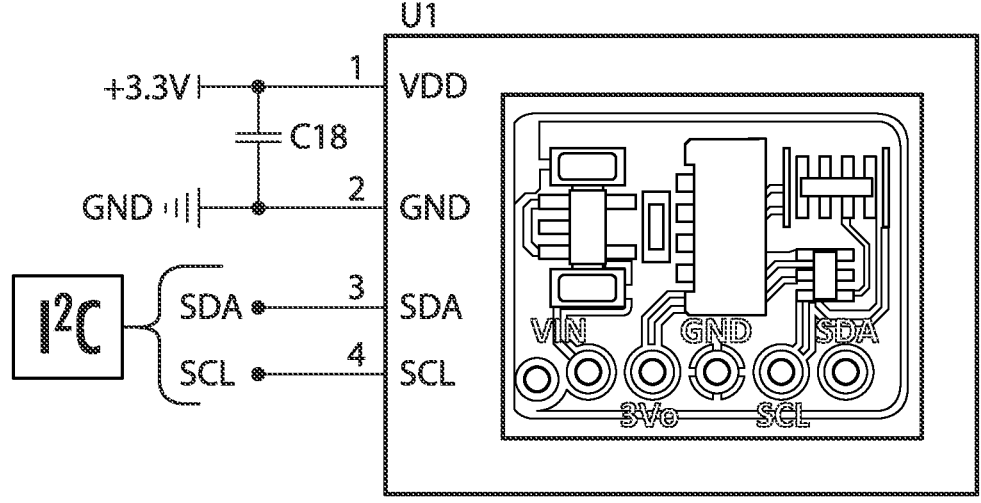
FIG. 5 is a schematic diagram of an example of an electronic illuminator's ambient light sensor chipset.

Turning now to FIG. 5, a schematic diagram of an example of an electronic illuminator's ambient light sensor chipset. There are three main types of ambient light sensors, namely, photodiodes, photonic ICs, and phototransistors. In principle they work along the same lines of converting light to voltage or current, and using the voltage or current for modes of operation. Typically, light enters the photodiode, wherein a thin layer allows photons to pass through it into a depletion region where a pair of electron holes are formed. The electric field across the depletion region causes electrons to be swept into an N layer. In some aspects, the ambient light sensor provides linear response over a wide dynamic range from 0.01 lux to 64,000 lux. The lux (symbol: lx) is the SI derived unit of illuminance, measuring luminous flux per unit area. It is equal to one lumen per square meter. In photometry, this is used as a measure of the intensity, as perceived by the human eye, of light that hits or passes through a surface.

Illuminance is analogous to the radiometric unit watt per square meter, but with the power at each wavelength weighted according to the luminosity function, a standardized model of human visual brightness perception. Illuminance is a measure of how much luminous flux is spread over a given area. One can think of luminous flux (measured in lumens) as a measure of the total "amount" of visible light present, and the illuminance as a measure of the intensity of illumination on a surface. A given amount of light will illuminate a surface more dimly if it is spread over a larger area, so illuminance is inversely proportional to area when the luminous flux is held constant.

The illuminance provided by a light source on a surface perpendicular to the direction to the source is a measure of the strength of that source as perceived from that location. Like all photometric units, the lux has a corresponding "radiometric" unit. The difference between any photometric unit and its corresponding radiometric unit is that radiometric units are based on physical power, with all wavelengths being weighted equally, while photometric units take into account the fact that the human eye's image-forming visual system is more sensitive to some wavelengths than others, and accordingly every wavelength is given a different weight. The weighting factor is known as the luminosity function.

The lux is one lumen per square meter (1m/m2), and the corresponding radiometric unit, which measures irradiance, is the watt per square meter (W/m2). There is no single conversion factor between lux and W/m2. There exists a different conversion factor for every wavelength, and it is not possible to make a conversion unless one knows the spectral composition of the light. The peak of the luminosity function is at 555 nm (green); the eye's image-forming visual system is more sensitive to light of this wavelength than any other. For monochromatic light of this wavelength, the amount of illuminance for a given amount of irradiance is maximum: 683.002 lux per 1 W/m2; the irradiance needed to make 1 lux at this wavelength is about 1.464 mW/m2. Other wavelengths of visible light produce fewer lux per watt-per-meter-squared. The luminosity function falls to zero for wavelengths outside the visible spectrum.

For a light source with mixed wavelengths, the number of lumens per watt can be calculated by means of the luminosity function. In order to appear reasonably "white", a light source cannot consist solely of the green light to which the eye's image-forming visual photoreceptors are most sensitive, but must include a generous mixture of red and blue wavelengths, to which they are much less sensitive.

This means that white (or whitish) light sources produce far fewer lumens per watt than the theoretical maximum of 683.002 1m/W. The ratio between the actual number of lumens per watt and the theoretical maximum is expressed as a percentage known as the luminous efficiency. For example, a typical incandescent light bulb has a luminous efficiency of only about 2%. In reality, individual eyes vary slightly in their luminosity functions. However, photometric units are precisely defined and precisely measurable. They are based on an agreed-upon standard luminosity function based on measurements of the spectral characteristics of image-forming visual photoreception in many individual human eyes.

In the example of FIG. 5, an ambient light sensor, configured as an ambient light sensor subsystem is integrated into the rigid-flex printed circuit board. By integrating the ambient light sensor, the electronic illuminator possesses the ability to visualize or detect the connection of the fiber feed by determining environmental lux, and the change in lux once the fiber is configured. An increase of lux within the housing, without an increase in the lux externally to the electronic illuminator may single that the onboard LED is active, but transmission through the fiber optic cable is not occurring Similarly, with ambient lux increased, from powering on of the LED drivers, it may signal that the electronic illuminator is operating as intended.

In other aspects, there exists a translucent ring at the proximal location of the illuminator to detect the ambient light difference from that of the LED's of the electronic illuminator. In one aspect, the ambient light sensor is placed on a flexible region of a RF-PCB in a location that is shaded from luminance of the fiber source. If the ambient light sensor detects ambient light with no fiber attached it can switch the microcontroller into low power mode. The ambient light sensor, in other aspects, assists with power control and sleep wake. In other aspects, the ambient light sensor detects errors within the LED or within the electronic illuminator. The ambient light sensor, in additional embodiments is equipped to detect occlusion of the signal of the electronic illuminator and to alert or otherwise inform users of an issue with the electronic illumination system.

Figures 6, 7:
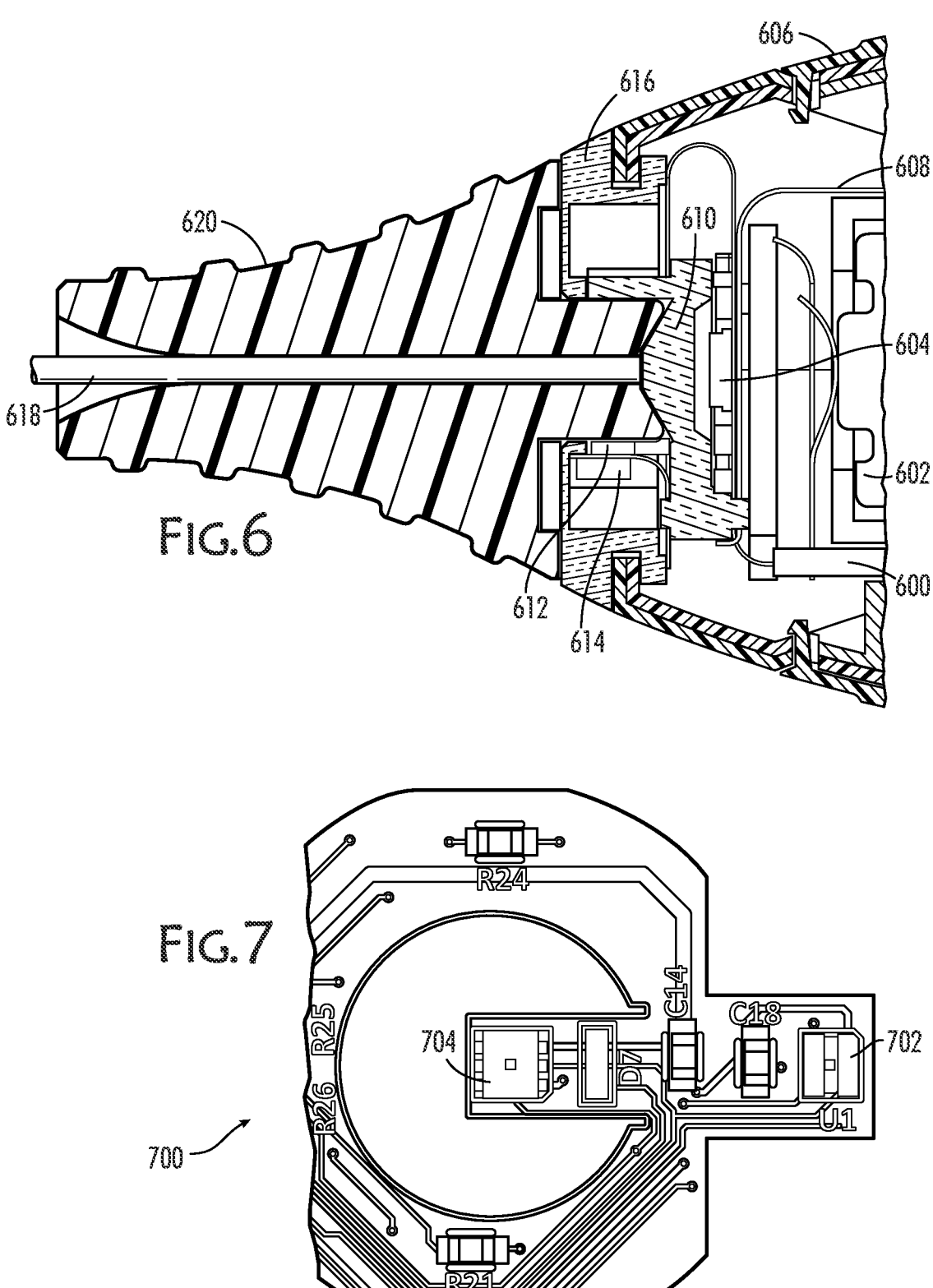
FIG. 6 is an illustration of an example of an electronic illuminator in cross section, disclosing the ambient light sensor configuration within the electronic illuminator.
FIG. 7 is an illustration of an example of an electronic illuminator's Rigid-Flex PCB, wherein the flex portion is disclosed with the ambient light sensor and the cap color detection assembly.

Referring now to FIG. 6, an illustration of an example of an electronic illuminator in cross section, disclosing the ambient light sensor configuration within the electronic illuminator. In the example, the ambient light sensor is configured in a region shaded from the LED 604 of the electronic illuminator. The ambient light sensor 614 is directed to receive lux or light from the environment through the translucent ring 616. In additional embodiments, the translucent ring 616 may have a filter to shade certain lux ranges so as to enable optimal performance. In other embodiments the translucent ring 616 may be non-translucent and have a window to the exterior for accumulating environmental lux as part of a power savings algorithm and automatic adjustment of LED power. For example, if the ambient light sensor 614 detects ambient light with no fiber attached it can switch the microcontroller or MCU into low power mode by communicating across the PCB 600. The ambient light sensor 614, in other aspects, assists with power control and sleep wake functionality, as well as instructing with other assemblies the proper usage by identifying whether or not the luminosity is enough to impact the environmental lux. When the power source is a battery 602, the algorithm may have conservative parameters versus connected directly to a power source such as a wall outlet. In other aspects, the ambient light sensor detects errors within the LED or within the electronic illuminator by detecting no light is emitting through the lens 610. The ambient light sensor, in additional embodiments, is equipped to detect occlusion of the signal of the electronic illuminator and to alert or otherwise inform users of an issue with the electronic illumination system.

Continuing, in FIG. 6, the R/G/B sensor 612 forming the cap color detection assembly is facing towards the receiving orifice of the fiber 618 and fiber funnel cap 620. The R/G/B sensor being equipped to read the outer surface of the inserted portion of the fiber funnel cap 620. Further, the R/G/B sensor is able to detect the color of the fiber funnel cap 620 for instructing the MCU to power LED drivers for a specific color or for other computational routines. The assemblies mentioned herein may generate heat, the internal heat sink 608 is positioned across those components and in thermal communication with the external heat sink 606 that in this example forms part of the housing of the electronic illuminator.

Referring now to FIG. 7, an illustration of an example of an electronic illuminator's Rigid-Flex PCB 700, wherein the flex portion is disclosed with the ambient light sensor 702 and the cap color detection assembly configured with an R/G/B sensor 704. The cap color detection assembly having the capability to read the cap color of a fiber funnel cap, to program the LED power drivers to illuminate a specific range of LED light to match the fiber funnel cap. In one aspect, the RGB sensor may be color light sensing with an IR blocking filter and with high sensitivity. Example manufacturers include Misumi™, Excelitas™, ams™, and include low power options with high sensitivity.

Examples of benefits and features for an R/G/B Sensor are disclosed in the table below:

| R/G/B Sensor | |
| --- | --- |
| Benefits | Features |
| Enables accurate color and light sensing measurements under varying lighting conditions by minimizing IR and UV spectral component effects | Red, Green, Blue (RGB), and Clear Light Sensing with IR blocking filter Programmable analog gain and integration time 3,800,000:1 dynamic range Very high sensitivity |
| Programmable interrupt pin enables level-style interrupts when pre-set values are exceeded, thus reducing companion micro-processor overhead | Maskable interrupt Programmable upper and lower thresholds with persistence filter |
| Enabling a low-power wait-state between RGBC measurements to reduce average power consumption | Power management Low power - 2.5 µA sleep state 65 µA wait state with programmable wait state time from 2.4 ms to >7 seconds |
| Digital interfaces are less susceptible to noise | I²C fast mode compatible interface Data rates up to 400 kbit/s Input voltage levels compatible with VDD or 1.8 VBUS |

In one aspect, an R/G/B sensor, as part of the cap color detection assembly is configured to read a multiple band code, wherein the bands may be coded or preprogrammed within the MCU to illuminate at a specific spectrum, such as to produce a specific color of light. The multiple band code may be transcribed as rings on a fiber side cap or along the fiber line, that when engaged with the electronic illuminator allows reading of the multiple band code and transmission from the cap color detection assembly to an MCU for signaling or communicating to the LED power drivers.

Figure 8:
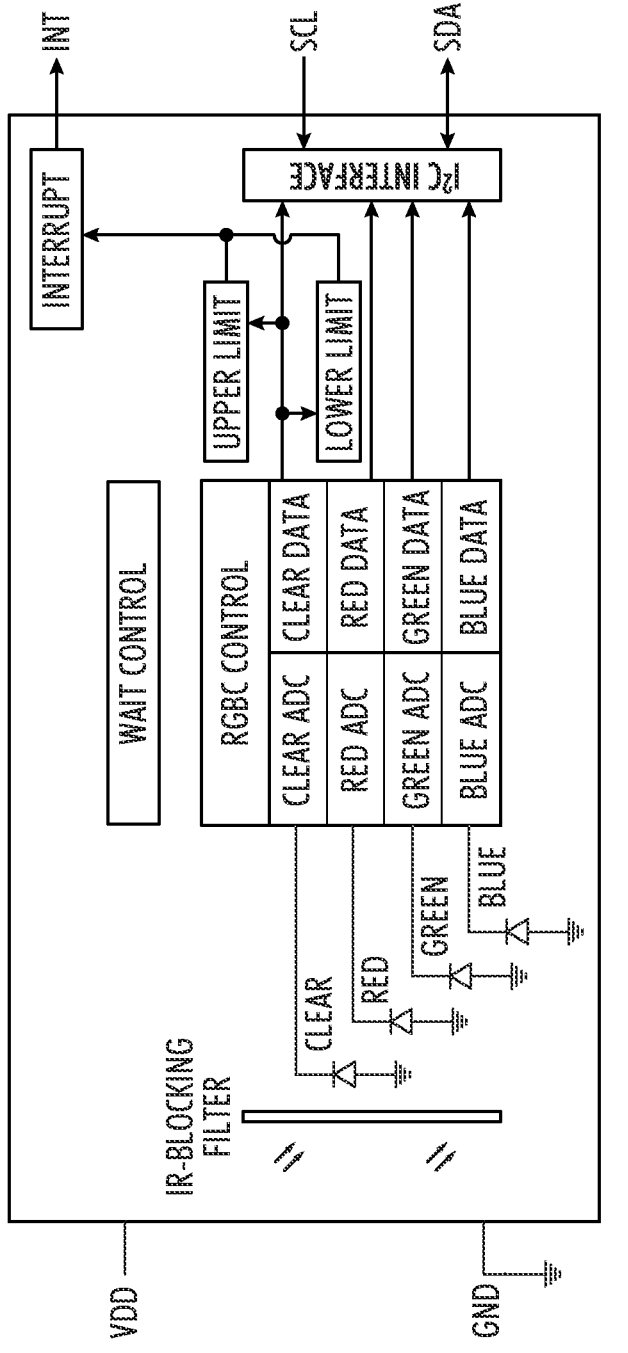
FIG. 8 is a block diagram of an example of an electronic illuminator's cap color detection assembly.

Referring now to FIG. 8, a block diagram of an example of an electronic illuminator's R/G/B sensor forming a cap color detection assembly. In the block diagram, the R/G/B control stack shows the architecture of the integrated circuit. Further, the R/G/B sensor is in interface communication with an MCU on a RF-PCB. The configuration is one of many, other examples may include additional components or configurations. For example, a multiple band code reader may contain additional elements.

In one aspect, a cap color assembly utilizes an R/G/B sensor to identify the cap color, wherein once acquired, communicates with an MCU which in turn instructed LED power drivers to illuminate for the specific color. In other aspects, a cap color detection assembly may be coded to specific instructions, such as to illuminate with a pattern, or to indicate expected luminosity outside of the ambient light sensor, to play an audio signal, or other cognitive aspect such as identifying with medical fluid treatment. In one aspect, a red cap or red band pattern may be programmed for blood products, or blood infusion. Whereas a green cap or green band pattern may be programmed for nutrients, and blue for saline, these are but a few possibilities with the systems and methods disclosed herein.

Figure 9:
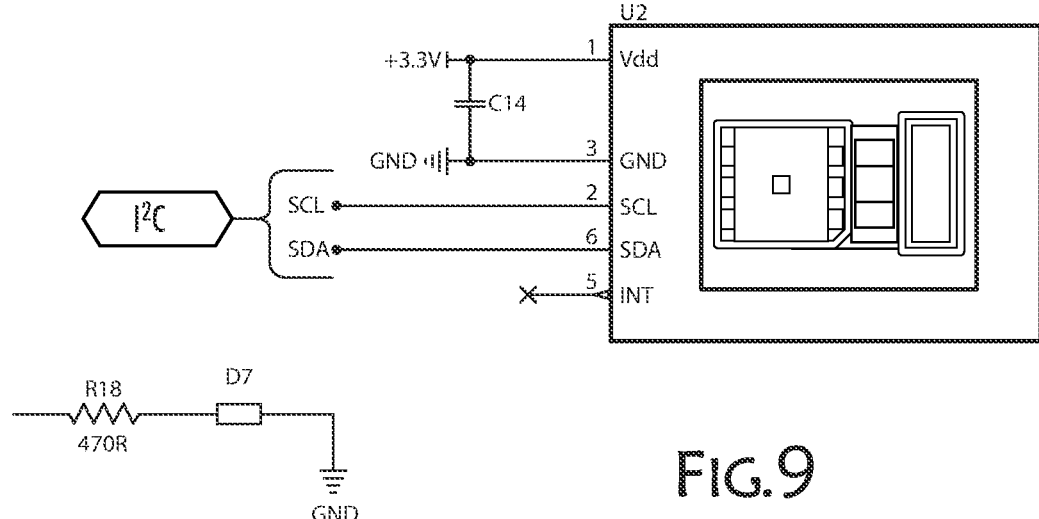
FIG. 9 is a schematic diagram of an example of an electronic illuminator's R/G/B sensor forming a part of the cap color detection assembly.

Referring now to FIG. 9, a schematic diagram of an example of an electronic illuminator's R/G/B sensor forming a part of the cap color detection assembly. In the example of FIG. 9, a schematic for one embodiment of an R/G/B sensor is disclosed. The MCU on the RF-PCB in communication through the I²C interface. In one aspect the cap color detection sensor minimizes IR and UV spectral component to product accurate color measurements. In another aspect the cap color detection detects the cap color of the funnel, or simply the cap on the fiber line. In other aspects the cap color detection sensor detects the color of the fiber side funnel and registers the color with the microcontroller or MCU, wherein the microcontroller determines what color the cap is made of and to what fiber cable the light color, or pattern should be emitted. The cap color detection sensor is enabled to scan for accurate color and ambient light sensing under varying conditions, ranging from ICU room lighting to patient care and resting state lighting. Furthermore, the cap color may serve as a watermark, proprietary colors may be selected, and or techniques of encoding the caps with color properties for counterfeiting prevention and authentication. Furthermore, the cap color detection sensor is capable of SKU identification, identifying aspects of readable codes such as bar codes, band codes, color codes or patterns. Such identification allows for authenticating and verifying medical equipment, which in turn helps reduce risk of patient harm, and allows the system to operate in normal fashion.

Figure 10:
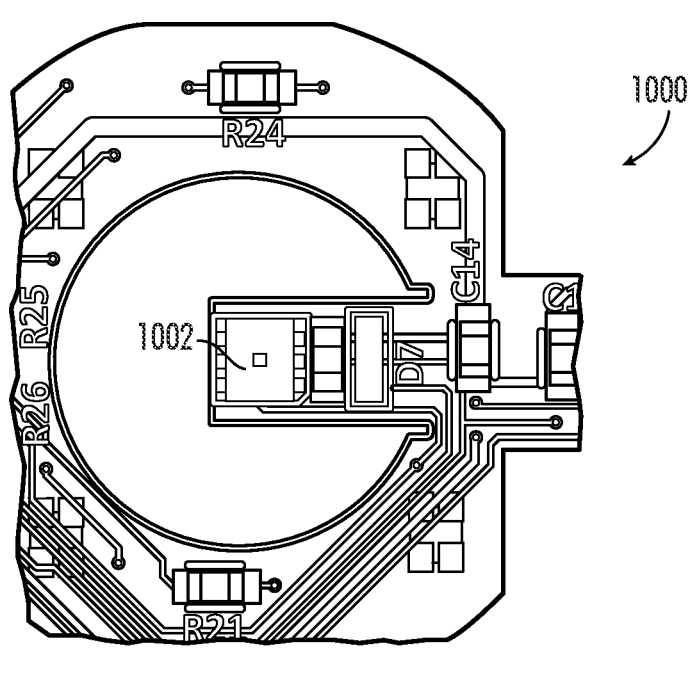
FIG. 10 is an illustration of an example of an electronic illuminator's Rigid-Flex PCB, wherein the flex portion is disclosed with the cap color detection assembly.

Referring now to FIG. 10, an illustration of an example of an electronic illuminator's Rigid-Flex PCB, wherein the flex portion is disclosed with the cap color detection assembly 1000. In one aspect the R/G/B sensor 1002 has an IR filter and white LED module. An example of an R/G/B sensor is the TCS34725, manufactured by TAOS™ (Texas Advanced Optoelectronic Solutions). In one aspect the R/G/B sensor 1002 returns and processes analog to digital values for a sensed object, such as a cap or band pattern. Further, in some aspects, the R/G/B sensor 1002 of the cap color detection assembly 1000 also allows for ambient light sensing for functions such as power savings, in use, security, and authentication. In one aspect the R/G/B sensor 1002 contains an 3×4 photodiode array and four analog to digital converters that integrate the photodiode, data registers, a state machine, and an I²C interface.

In additional aspects a watermark, or color array, for a series of color bands may be used for security and authentication. In one aspect a series of banded color codes is placed and read by the cap color detection assembly within the electronic illuminator. If the color code is a match the electronic illuminator functions, if the color code is not a match the electronic illuminator provides notification. Notification can consist of a signal or transmission, or other notification that the fiber is either not genuine, or is inserted incorrectly, or there is a failure within the system. Additionally, in another aspect, the color bands or watermark may also provide input to the electronic illuminator regarding the LED transmission color to illuminate the fiber line with.

Figure 11:
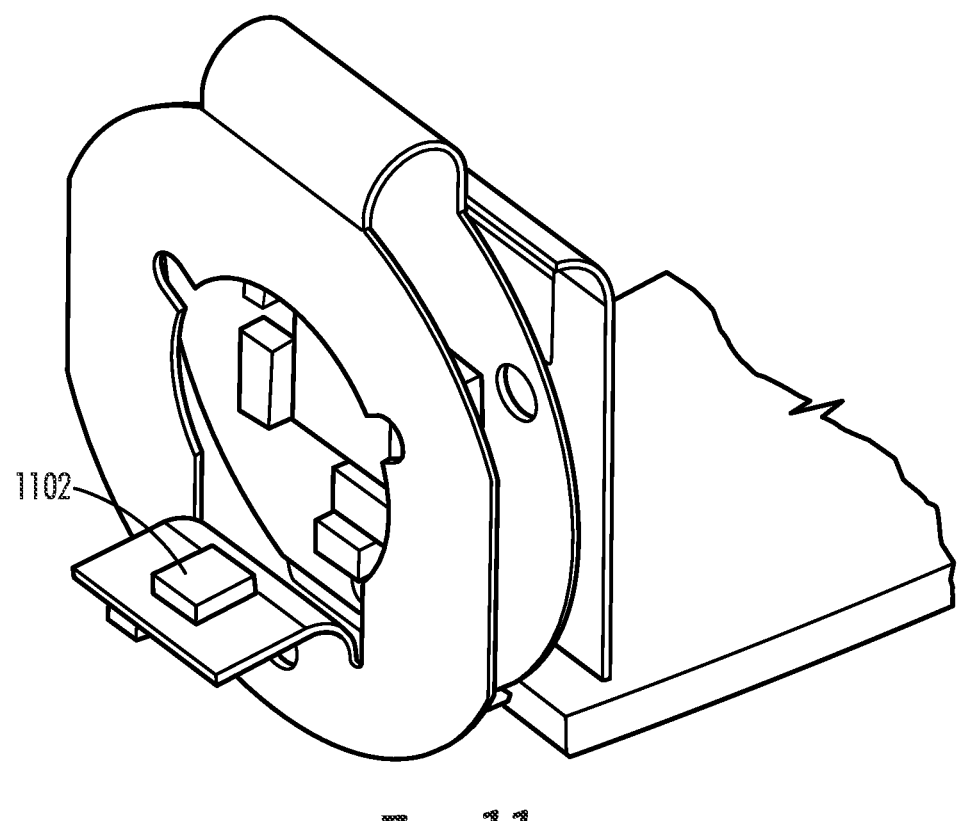
FIG. 11 is an illustration of an example of an electronic illuminator, disclosing the cap color detection assembly configuration within the electronic illuminator.

Referring now to FIG. 11, an illustration of an example of an electronic illuminator, disclosing the cap color detection assembly configuration within the electronic illuminator. In the example view the cap is disclosed wherein it is configured with the electronic illuminator. The R/G/B sensor 1102 of the cap color detection assembly is configured to interface with the cap of the fiber optic line. Further, the position of the R/G/B sensor 1102 also accounts for reading of a unique band code or code on the cap side or funnel cap that codes for a specific light, or for authentication, or additional features as programmed within the system. In one aspect, the multiple band code identifies red and the power driver of a red LED is turned on.

Figure 12:
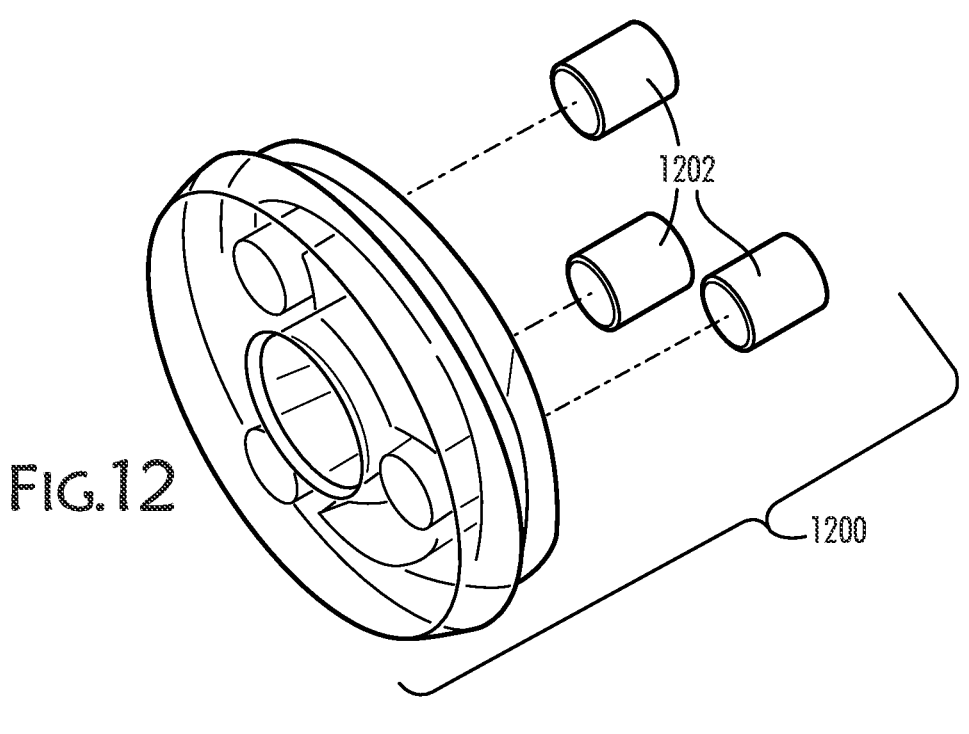
FIG. 12 is an illustration of an example cap and magnet assembly for an electronic illuminator, the configuration provides aspects of the fiber detection assembly.

Referring now to FIG. 12, an illustration of an example translucent cap 1200 and magnet array 1202 for an electronic illuminator, the configuration provides aspects of the fiber detection assembly. The cap may be translucent and work in coordination with the optical sensor disclosed above, for sensing environmental light and light leakage from the side scattering fiber optic line. The translucent cap 1200 is fitted to the electronic illuminator forming a part of the housing. Disclosed within FIG. 12 is positioning for a plurality of magnets to form a magnetic field. Such field may be utilized for authentication, activation, security, and transmission of information utilizing a specific flux key or signature.

Figure 13:
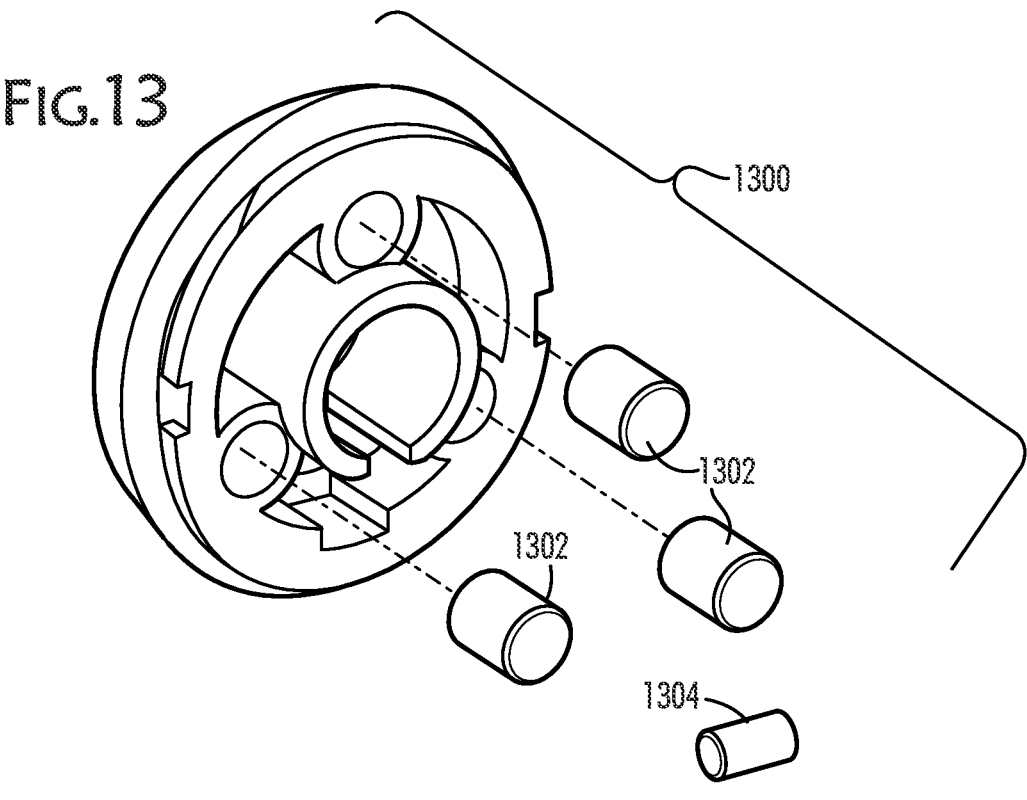
FIG. 13 is an additional illustration of an example cap and magnet assembly with a steel bar for an electronic illuminator, the configuration provides aspects of the fiber detection assembly.

Similarly, referring to FIG. 13, an additional illustration of an example translucent cap and magnet assembly 1302 with a steel bar 1304 for an electronic illuminator. In the example the configuration provides aspects of the fiber detection assembly 1300. In one aspect, the translucent cap may not be translucent, it may be opaque with a filter or may have a window within it for the ambient light sensor. In other examples the translucent cap is a general cap for accepting the magnet assembly 1302. The steel bar 1304 provides tuning of magnetic field to allow for tuning of specific fields, allowing for more than authentication, but having different flux keys or signatures result in different effects, such as programmed to a specific color, or pattern for the LED driver. With regard to authentication, the steel bar 1304 may also be a magnetic bar and it is utilized in tuning, the electronic illuminator may also not require a steel bar 1304 and the system may operate with a three dimensional magnetic flux based on the magnet assembly 1302, wherein the key or signature is determined by the metallic plate on the funnel cap being engaged with the electronic illuminator.

Figure 14:
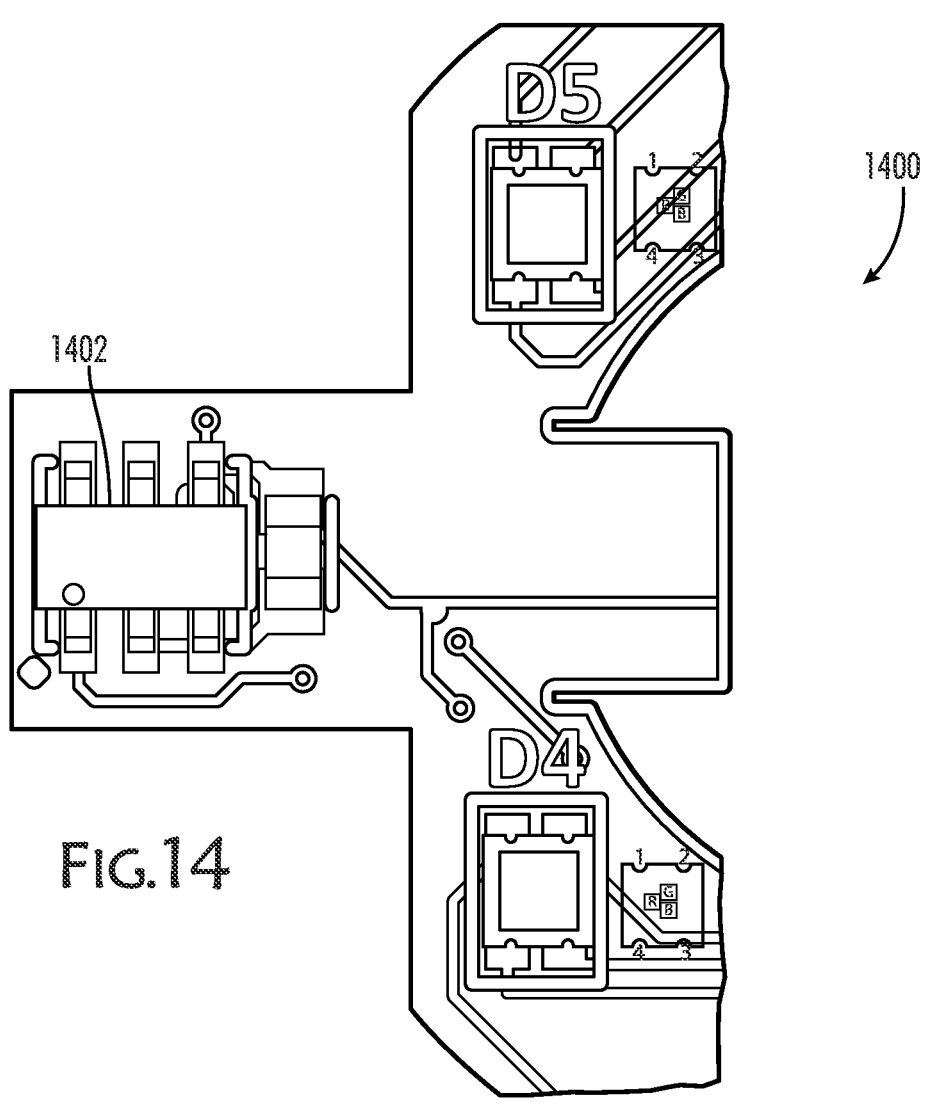
FIG. 14 is an illustration of an example fiber detection assembly, wherein the Rigid-Flex PCB is disclosed with a Hall sensor.

Referring now to FIG. 14, an illustration of an example fiber detection assembly, wherein the Rigid-Flex PCB 1400 is disclosed with a hall sensor 1402. A Hall-effect sensor also known as a Hall sensor is a device that measures the magnitude of a magnetic field. A Hall sensor's output voltage is directly proportional to the magnetic field strength through it. Hall sensors are used for proximity sensing, positioning, speed detection, and current sensing applications. Frequently, a Hall sensor is combined with threshold detection, so that it acts as and is called a switch. Commonly seen in industrial applications, Hall sensors are also used in consumer equipment and medical applications; for example, some computer printers use Hall sensors to detect missing paper and open covers. They can also be used in computer keyboards, an application that requires ultra-high reliability. An example of a Hall sensor is the US1881 by Melexis™ that is based on mixed signal CMOS technology. In one aspect, the Hall sensor is equipped with high magnetic sensitivity, has an operating voltage of 3.5V up to 24V, and a low current consumption.

In one aspect, the Hall sensor 1402 on the electronic illuminator detects the presence of the fiber line through a series of magnets placed on the front cap of the electronic illuminator. In one embodiment the electronic illuminator creates a 3D magnetic flux density that is capable of sensing to +/−160 mT. In other embodiments a range exists over +/−160 mT. The Hall sensor is equipped with a programmable flux resolution to 65 uT. Therefore, enabling position detection and X-Y angular and fiber orientation and measurements. The 3d magnetic flux is also known as a magnetic flux key or signature, and such signature can be used for authentication and verification of the illuminating infusion line or the fiber line. Further, in other aspects, the Hall sensor 1402 controls the power supply and sleep wake functionality by detecting presence of the fiber funnel cap. In this aspect, when the fiber funnel cap is not attached, the Hall effect sensor will signal to the electronic illuminator to place it in sleep mode. The hall sensor 1402 is further equipped to provide energy saving aspects by controlling functionality of on/off, sleep/wake, rest state of a microcontroller or other processing unit, including turning on or off the assemblies that may draw from the power source. In other aspects, the Hall sensor 1402 enables device security through detection of a flux key or signature, by detecting the magnetic flux of the metal plate on the fiber funnel cap, with the field generated by the magnetic assembly on the electronic illuminator.

In the example of FIG. 14, in one aspect of the electronic illuminator a plurality of magnets for a magnetic field that can be registered by onboard sensors, such as a hall sensor, the flux may be used to verify the device is in use or other aspects such as security and authentication. In such a scenario the magnetic field is tuned to a flux key or signature so as to authentic the device. In one aspect a steel pin is utilized to adjust the flux field, in another a different material capable of disturbing magnetic force is used. In one aspect the steel pin is set to match the signature of a specific funnel color of illuminating fiber optic line. In another aspect the steel pin or other magnetic flux disturbing device is positioned for specific voltage readings from the Hall sensor. In such an embodiment authenticating the various attachment fiber optic lines can be observed. Further, in additional embodiments the sleep wake function of the microcontroller may be activated by the Hall sensor, thus allowing power conservation.

Continuing with FIG. 14, in one aspect the fiber line cap or fiber line funnel may be a specific color that designates the color of LED light the LED power driver will illuminate within the electronic illuminator. The fiber side cap or fiber funnel cap or fiber cap is located proximal to the electronic illuminator, and at the opposite end of where the fiber line terminates. The distal end of the fiber line may have a protective proximal cap. The fiber line cap is equipped with a metal plate to match and verify a specific signature (flux key, flux signature) wherein the electronic illuminator's Hall sensor, as part of the fiber line detection assembly, can sense and acknowledge the signature. In some aspects, the fiber side cap, equipped with a magnetic plate is used for authentication and verification. In other aspects, the fiber side cap is utilized for providing instruction to the electronic illuminator, such as color code tuned to a specific flux key, or other instructions such as pulsed light, cleaning sequence or otherwise. In additional aspects, an antenna may be placed on the proximal cap cover of the fiber line, in which the microcontroller may send a radio pulse and receive a signal, this embodiment may be tied to an optical power sensor, or the microcontroller, or both.

Figure 15:
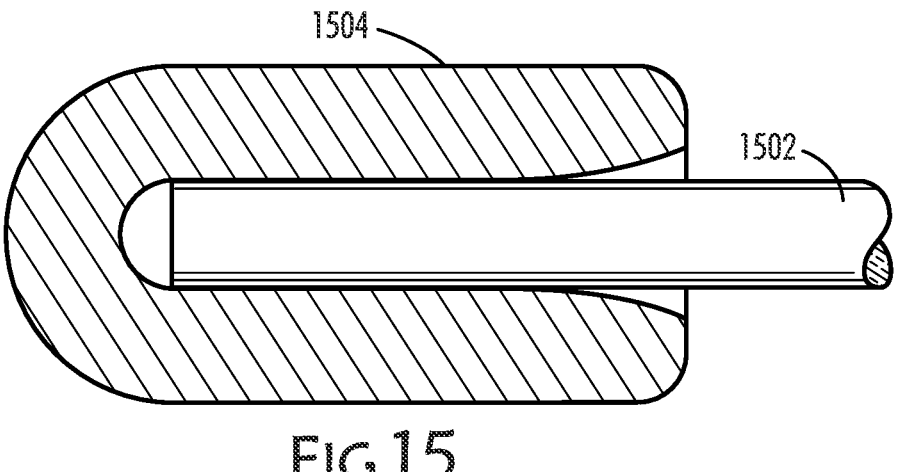
FIG. 15 is an illustration of a distal end cap or protective end cap on a side scattering fiber optic line.

Referring now to FIG. 15, an illustration a distal end cap of a side scattering or side emitting fiber optic line. In the example the distal end cap 1504 also known as a protective end cap for the fiber optic line 1502, has a polished surface that is highly reflective of light. The polished surface allows for reflection, similar to a mirror, wherein the programmed MCU may initiate a sequence of flashes for authentication or verification. Additionally, a routine of pulsed light may be used for signaling the length of the fiber optic line 1502 for regulating intensity of the LED and thus controlling power drivers and saving power. This may work in coordination with the ambient light sensor, disclosed previously, to regulate power output based on the environmental light and length of the fiber optic line 1502.

Continuing, the protective end cap 1504, with a polished surface, or a surface coated with a reflective material, is also made of a resilient material such as a hard plastic (polymeric material) or metal that allows for protection of the fiber optic line 1502 so it does not fray or come into contact with patients. Additionally, the protective end cap 1504 is smooth and made to be non-abrasive and easy to clean, with no openings or otherwise which allows for prevention of bacterial growth and reusability.

Further, the protective end cap 1504 may be equipped with a one line antennae that is utilized for communicating over radio frequency, thus adding an additional layer of communication to the fiber optic line. The one line antennae acts as a passive wireless antenna and may be used for determining fiber optic line length or for verification and authentication. In this aspect, the electronic illuminator may ping or bounce a radio wave off the antennae and receive a response, wherein the time duration allows for estimation of the length of the fiber optic line.

Figures 16A, 16B, 16C:
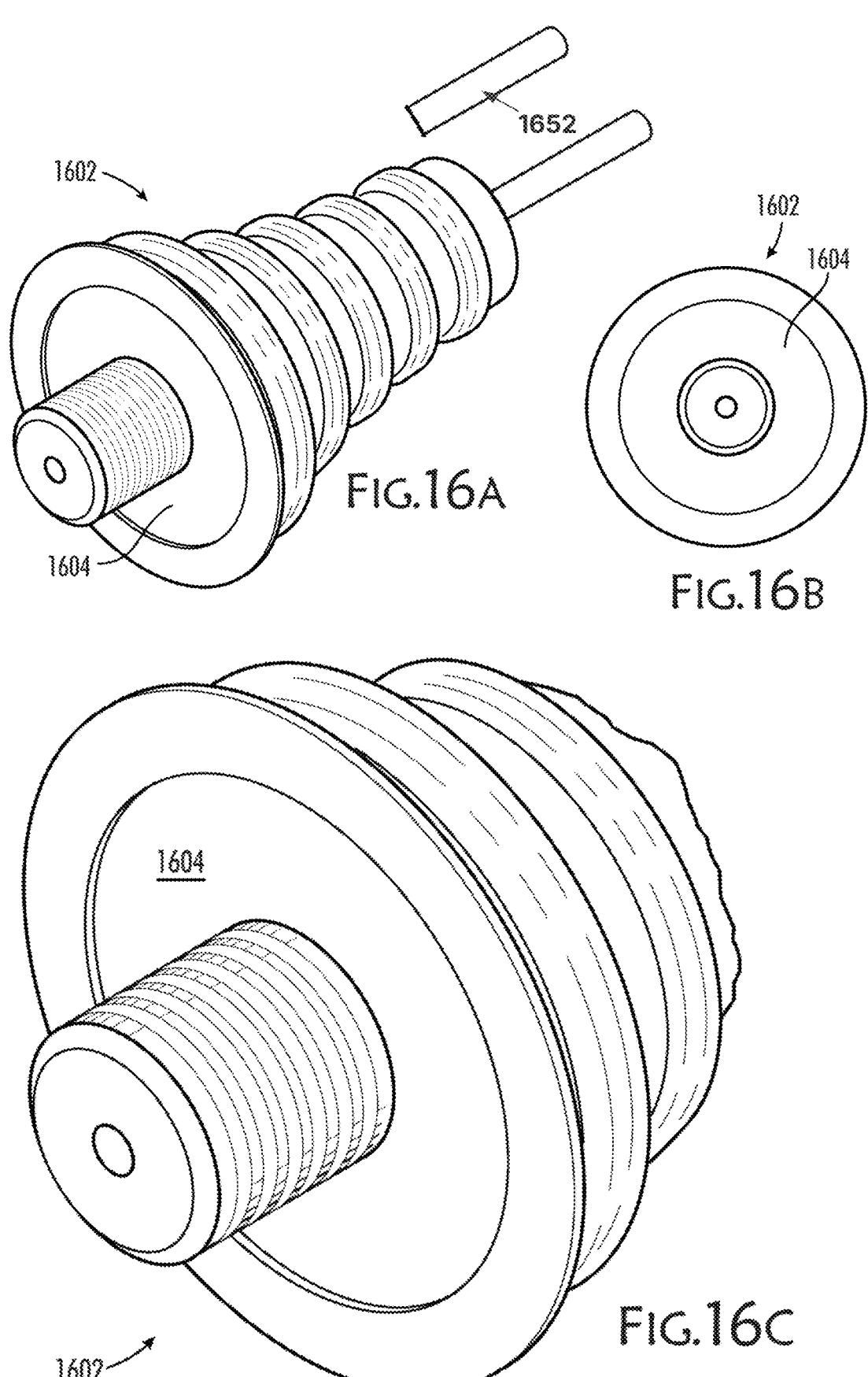
FIGS. 16A-C are illustrations of a fiber funnel cap that is designed to operatively engage with an electronic illuminator.

Referring now to FIGS. 16A-C, disclosed are various aspects of a fiber funnel cap 1602 that is designed to engage with the electronic illuminator. When engaging or configuring, the fiber funnel cap connects through the translucent ring to the lens, for transmitting light along the side scattering or side emitting fiber optic line (e.g., of a medical infusion line 1652). The fiber funnel cap 1602 may also be configured with a metal plate 1604 that may be utilized for magnetically locking the cap into the electronic illuminator. The fiber side funnel may also configure into place within the electronic illuminator based on ridges that configure to the housing to hold the end cap within the electronic illuminator near the lens and LED assembly. Further, the metal plate 1604 may also be used for authentication and verification in coordination with the fiber detection assembly and the onboard Hall sensor. In this regard, the metal plate 1604 is characterized by a specific angle vector relative to the onboard magnets of the electronic illuminator, thus creating a signature or key. As the fiber funnel cap approaches the electronic illuminator a change in voltage is registered in the Hall sensor on the onboard fiber detection assembly, once configured a specific voltage and flux will register, authenticating the side scattering fiber optic cable. For example, as the fiber funnel cap is engaged the Hall sensor may read an increase in voltage and a final voltage level may indicate the flux key or signature.

Continuing, the fiber funnel cap 1602 may come in a variety of colors and the color is detected by the cap color detection assembly, wherein the MCU may power an LED driver to the specific cap color. Further, the fiber funnel cap 1602 may be equipped with bands, such as a multiple band code, that allows for the R/G/B sensor of the cap color detection assembly to read the bands and transmit to the MCU a signal for the color to illuminate. Therefore, the fiber optic line, including the fiber funnel cap may be "programmed" from manufacture to illuminate a specific LED driver within the electronic illuminator. Further, the multiple band pattern may be used for authentication, as a set number of bands or color code, or other parameter may be etched or otherwise encoded onto the fiber funnel cap 1602 allowing for authentication by the electronic illuminator based on the band count, pattern, or other code.

Figure 17:
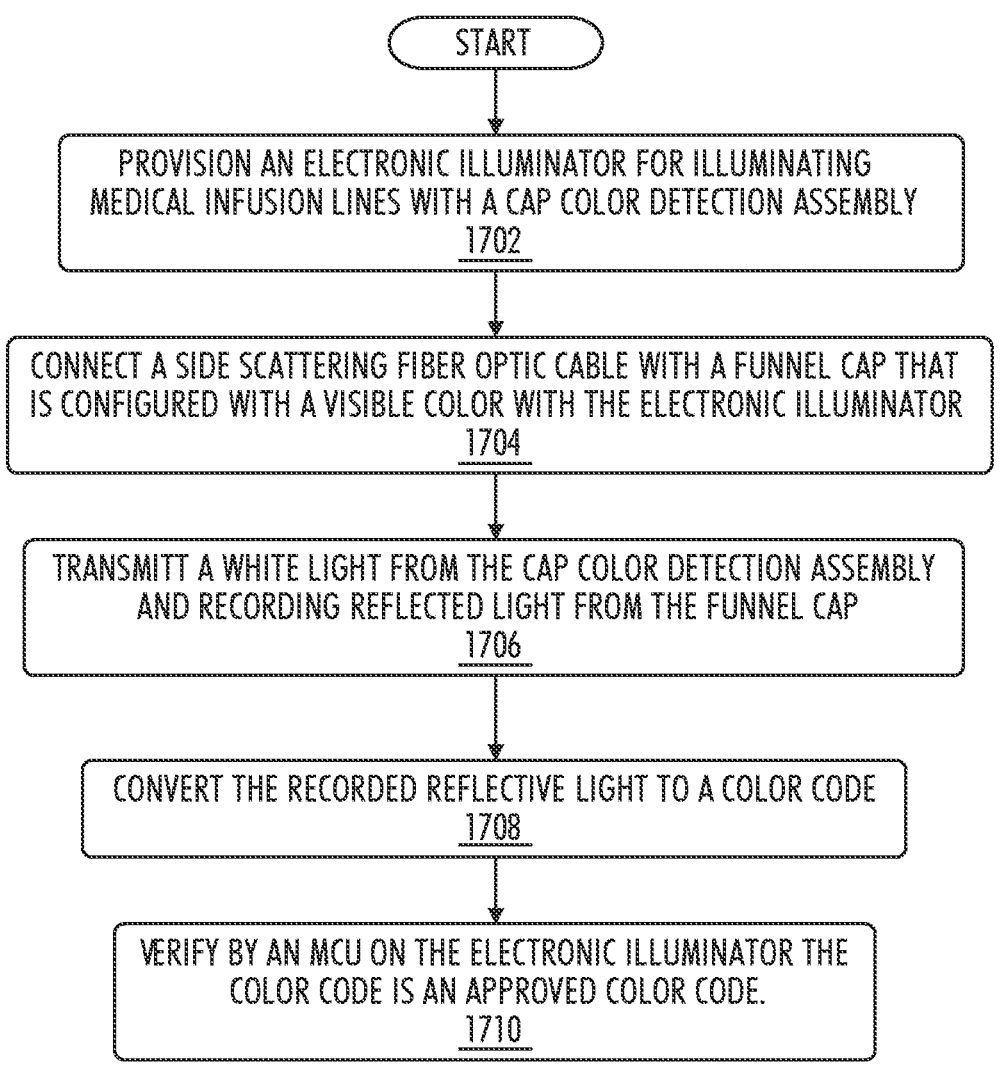
FIG. 17 is a flow chart of an example method for authenticating medical infusion lines with a cap color detection assembly.

Referring now to FIG. 17, a flow chart of an example method for authenticating medical infusion lines with a cap color detection assembly. In the example, an electronic illuminator is provisioned that is equipped with a cap color detection assembly 1702. The cap color detection assembly is configured with a R/G/B sensor, and is positioned in line with the LED power driver and the location where a fiber funnel cap of the side scattering fiber optic cable is configured with the electronic illuminator. Next, the side scattering fiber optic cable with a funnel cap is connected or configured to the electronic illuminator by inserting it into the electronic illuminator 1704 and engaging so as though it cannot be removed without effort. The configuration may be physical based, or magnetic, or a combination of both, including ridges and or latches. Next, from a photoelectric sensor on the cap color detection assembly, a white LED is broadcasted or transmitted against the fiber funnel cap 1706, wherein the reflected light provides an analog signal that may be converted to a digital color code such as a hex code or R/G/B code by the cap color detection assembly 1708. Lastly, the onboard computing module or MCU or IC verifies the color code is an approved color code against a database or parameters defined and stored within the electronic illuminators storage device 1710. The electronic illuminator is capable of receiving updates, including new parameters for color codes, and allows configuration of color codes for specific infusion products. For example, a red funnel cap may be designated for blood products, and a blue funnel cap for hydration, such as saline products. In this regard, the authentication may also serve to verify the user's understanding of the infusion product along with the medical infusion lines, thus lowering the cognitive load and ensuring correct infusion.

Figure 18:
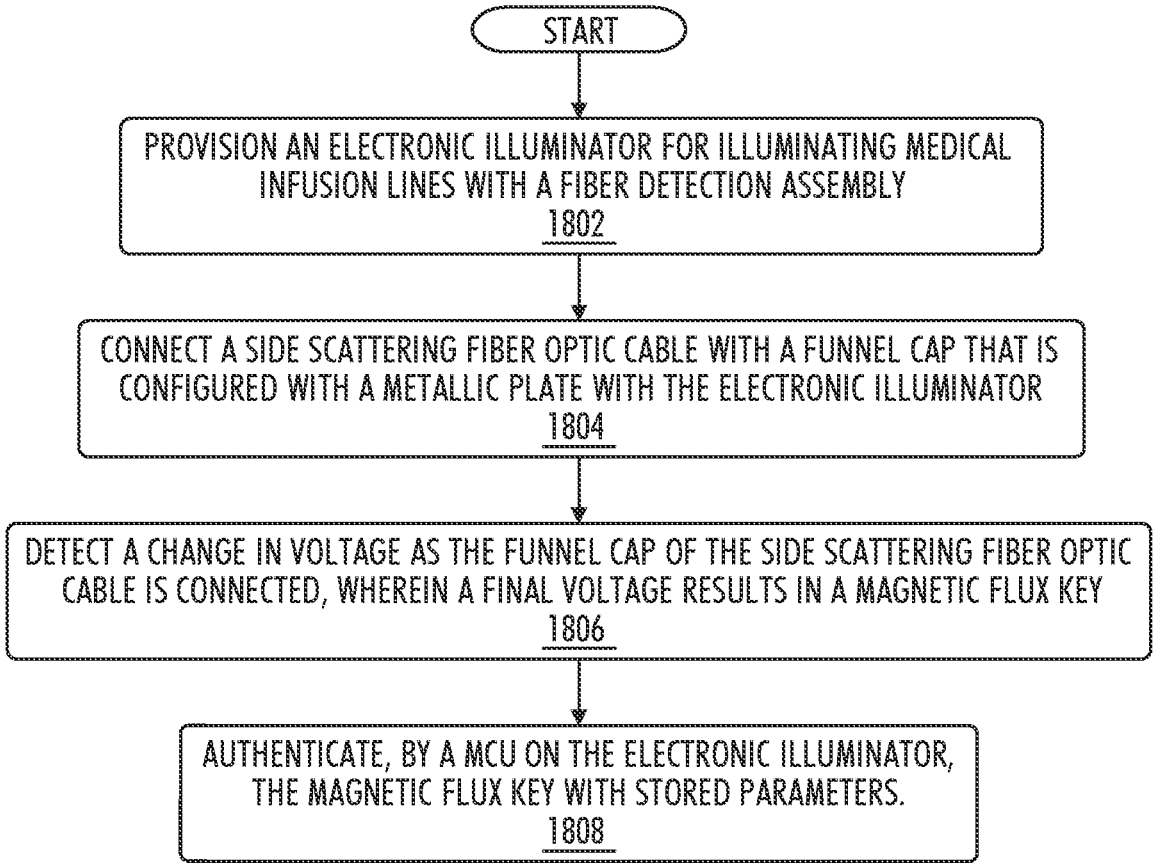
FIG. 18 is a flow chart of an example method for authenticating medical infusion lines with a fiber detection assembly.

FIG. 18 is a flow chart of an example method for authenticating medical infusion lines with a fiber detection assembly. In the example, an electronic illuminator is provisioned with a fiber detection assembly 1802. The fiber detection assembly comprising a hall effect sensor or hall sensor, wherein it detects a change in a magnetic field and reflects said change with either an increase or decrease in voltage. Next, a side scattering fiber optic cable with a funnel cap, the funnel cap including a metallic plate, such as a steel plate that has the capability to be influenced by magnetic force. The side scattering fiber optic cable with a funnel cap or proximal end cap is configured to the electronic illuminator so that light may pass down the length of the fiber optic cable 1804. As it is being connected, or once connected, the hall effect sensor detects a change in voltage and registers that change, due in part to the onboard magnets, a steel bar, and a steel plate on the funnel cap 1806. The registered voltage forms a flux key or signature from the change in the magnetic flux, wherein the specific reading may be verified and authenticated by the electronic illuminators on board computing system, or MCU 1808. The verification of the flux key or signature authenticates that the side scattering fiber optic line is manufactured correctly and conforms to standards for use with the electronic illuminator.

Figure 19:
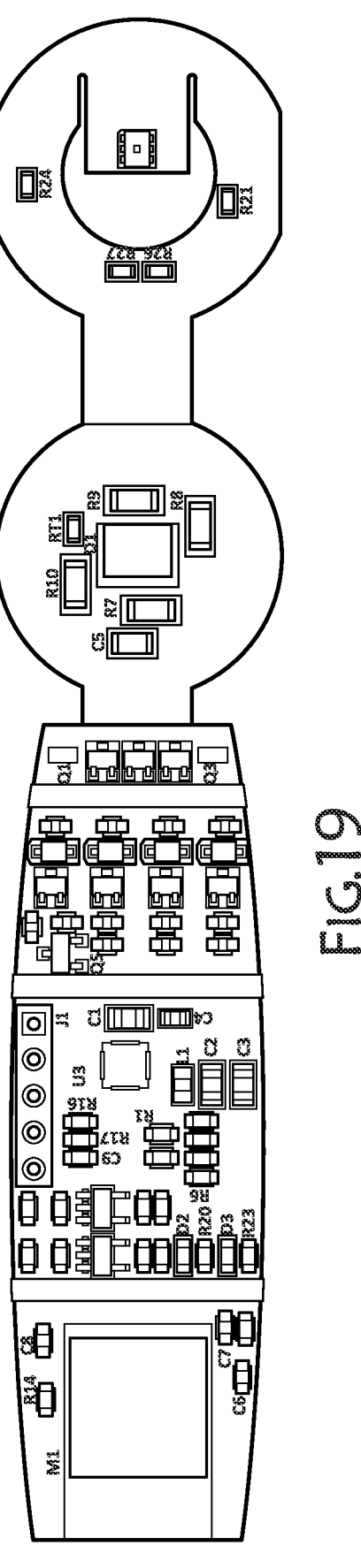
FIG. 19 is an illustration of an example PCB for authenticating medical infusion lines.

FIG. 19 is an illustration of an example PCB for authenticating medical infusion lines. In the example, a flex portion and a rigid portion are formed, wherein the flex portion may be folded unto itself and configured so that the R/G/B sensor of the cap color detection assembly may read the connected funnel cap of the side scattering fiber optic line, and that it may also further read a multiple band code or other code placed on the side of the protruded region that interfaces with the electronic illuminator Similarly, the fiber detection assembly, with the hall effect sensor may be configured on the flex portion of the PCB so as to move the proximity of the hall effect sensor as close as possible to the translucent ring with magnets and a steel bar, wherein the creation of a magnetic flux density is formed, and further when connected with the funnel cap and metallic plate, a change in voltage may be registered, or a hall effect sensor may register a change in the magnetic field.

Figure 20:
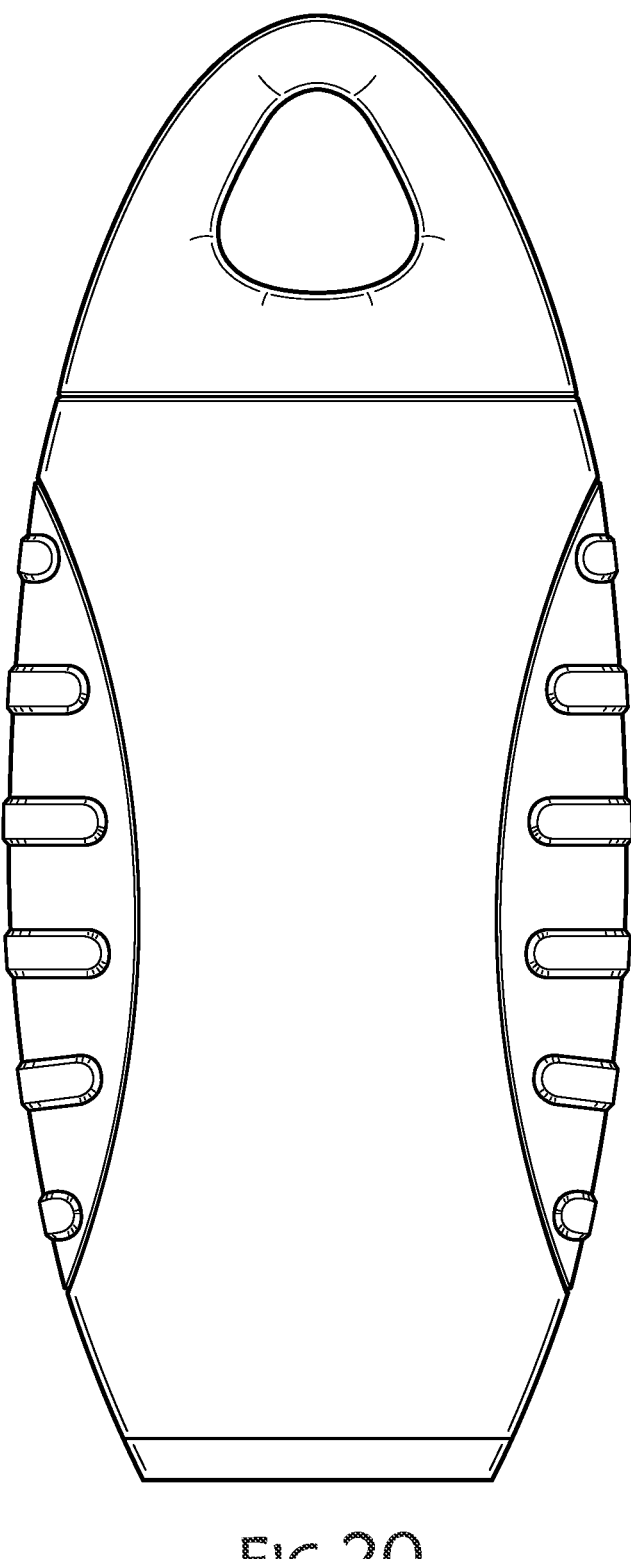
FIG. 20 is an illustration of an example housing for an electronic illuminator.
Figure 21:
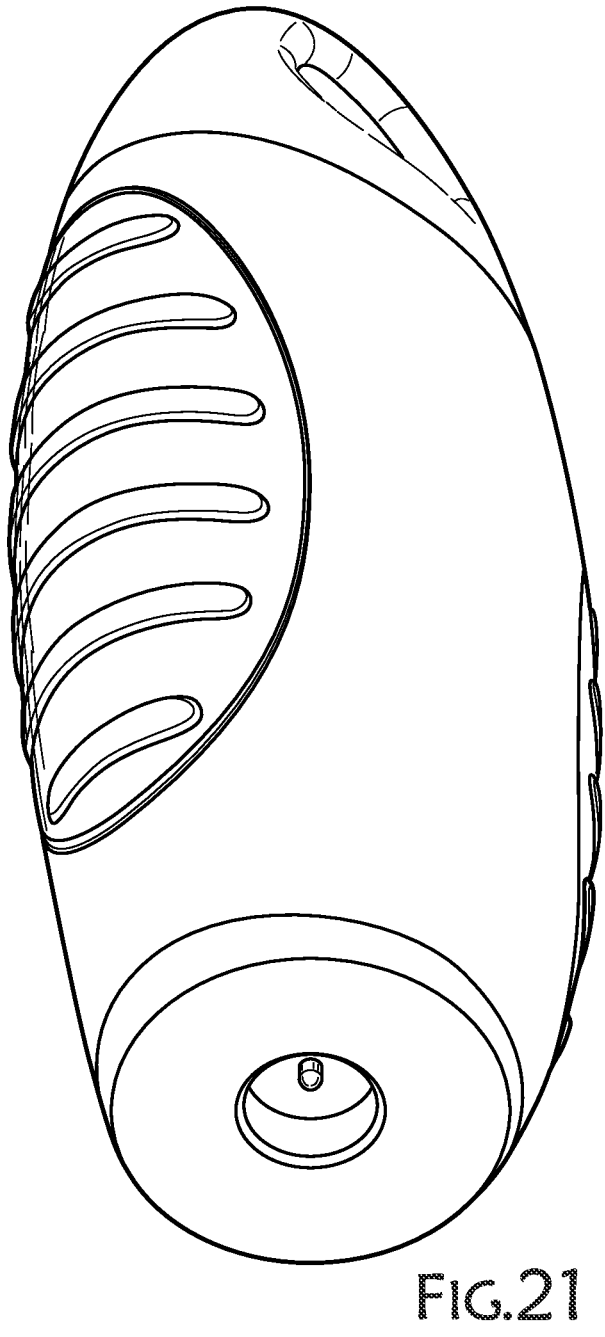
FIG. 21 is an additional view of an illustration of an example housing for an electronic illuminator.

FIGS. 20 and 21 are illustrations an example housing for an electronic illuminator. The provided examples disclose the electronic illuminator as well as opening for receiving the funnel cap of the side scattering fiber optic line. The housing provides thermal control through an outer heat sink, in configuration with an inner heat sink to help distribute heat to the environment from a compact form. Further, the housing is configured with dustproofing, shock proofing, and other benefits to handle extended use in critical care environments.

In other aspects the housing may be a medical infusion pump, wherein the contents of the various assemblies, such as the cap color detection assembly, the fiber detection assembly, and the ambient light sensor may be configured in the housing. In this example, the authentication methods remain the same, the power source may be a wall outlet or receive power from an onboard batter configured to the medical infusion pump.

IV. Embodiments

Certain implementations of systems and methods consistent with the present disclosure are provided as follows:

Implementation 1. A system for illuminated medical infusion line authentication, comprising: (i) an electronic illuminator, comprising: a cap color detection assembly; a fiber detection assembly; (ii) a side scattering fiber optic cable, comprising: a fiber funnel cap with a visible color at a proximal end and a metallic plate; and a protective end cap at a distal end.

Implementation 2. The system of implementation 1, wherein the fiber detection assembly is configured with a three dimensional magnetic flux density.

Implementation 3. The system of implementation 1, wherein the fiber detection assembly comprises a hall effect sensor.

Implementation 4. The system of implementation 1, wherein the fiber detection assembly is comprised of three magnets and a steel bar.

Implementation 5. The system of implementation 1, wherein the cap color detection assembly of the electronic illuminator detects color of the fiber funnel cap on the side scattering fiber optic cable.

Implementation 6. The system of implementation 1, wherein the cap color detection assembly comprises a photoelectric sensor.

Implementation 7. The system of implementation 1, wherein the cap color detection assembly comprises a RGB sensor.

Implementation 8. The system of implementation 1, wherein the cap color detection assembly comprises a color code band detection, wherein the funnel cap comprises a multiple band color code.

Implementation 9. A method for authenticating medical infusion lines, comprising: provisioning an electronic illuminator for illuminating medical infusion lines with a cap color detection assembly; connecting a side scattering fiber optic cable with a fiber funnel cap that is configured with a visible color with the electronic illuminator; transmitting a white light from the cap color detection assembly and recording reflected light from the fiber funnel cap; converting the recorded reflective light to a color code; and verifying by an MCU on the electronic illuminator the color code is an approved color code.

Implementation 10. The method of implementation 9, further comprising provisioning a multiple band code on the fiber funnel cap of the side scattering fiber optic cable.

Implementation 11. The method of implementation 10, further comprising transmitting the white light from the cap color detection assembly and recording reflected light from each band of the multiple band code.

Implementation 12. The method of implementation 11, further comprising converting the multiple band code to a color code.

Implementation 13. The method of implementation 12, further comprising verifying by the MCU on the electronic illuminator the multiple band color code is an approved color code.

Implementation 14. The method of implementation 9, further comprising alerting by the electronic illuminator that the side scattering fiber optic cable is authentic.

Implementation 15. A method for authenticating medical infusion lines, comprising: provisioning an electronic illuminator for illuminating medical infusion lines with a fiber detection assembly; connecting a side scattering fiber optic cable with a fiber funnel cap that is configured with a metallic plate with the electronic illuminator; detecting a change in voltage as the fiber funnel cap of the side scattering fiber optic cable is connected, wherein a final voltage results in a magnetic flux key; and authenticating, by a MCU on the electronic illuminator, the magnetic flux key with stored parameters.

Implementation 16. The method of implementation 15, further comprising alerting by the electronic illuminator that the side scattering fiber optic cable is authentic.

Implementation 17. The method of implementation 15, further comprising alerting by the electronic illuminator that the side scattering fiber optic cable is not authentic, and further disengaging an LED assembly on the electronic illuminator.

Implementation 18. The method of implementation 15, wherein detecting a change in voltage detects an increase in voltage as the fiber funnel cap connects with the electronic illuminator.

Implementation 19. The method of implementation 15, wherein provisioning an electronic illuminator with a fiber detection assembly provisions three magnets and a steel bar to calibrate a specific three dimensional magnetic field.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

Therefore, the following is claimed:

1. A method for authenticating medical infusion lines, comprising:

connecting a side scattering fiber optic cable with a fiber funnel cap having a visible color with an electronic illuminator that illuminates one or more medical infusion lines;

transmitting a white light from a cap color detection assembly of the electronic illuminator, and recording reflected light from the fiber funnel cap;

converting the reflected light to a color code; and verifying by a microcontroller (MCU) onboard the electronic illuminator that the color code is an approved color code.

2. The method of claim 1, wherein a multiple band code is on the fiber funnel cap of the side scattering fiber optic cable.

3. The method of claim 2, further comprising transmitting the white light from the cap color detection assembly and recording reflected light from each band of the multiple band code.

4. The method of claim 3, further comprising converting the multiple band code to a color code.

5. The method of claim 4, further comprising verifying by the MCU on the electronic illuminator the multiple band color code is an approved color code.

6. The method of claim 1, further comprising alerting by the electronic illuminator that the side scattering fiber optic cable is authentic.

* * * * *